United States Patent
Montchamp et al.

(10) Patent No.: US 8,877,957 B2
(45) Date of Patent: Nov. 4, 2014

(54) SYTHESIS OF P-CHIRAL COMPOUNDS

(71) Applicants: Jean-Luc Montchamp, Fort Worth, TX (US); Olivier Berger, Fort Worth, TX (US)

(72) Inventors: Jean-Luc Montchamp, Fort Worth, TX (US); Olivier Berger, Fort Worth, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

(21) Appl. No.: 13/912,393

(22) Filed: Jun. 7, 2013

(65) Prior Publication Data

US 2013/0331594 A1    Dec. 12, 2013

Related U.S. Application Data

(60) Provisional application No. 61/657,944, filed on Jun. 11, 2012.

(51) Int. Cl.
  *C07F 9/48*     (2006.01)
  *C07F 9/572*    (2006.01)
  *C07F 9/32*     (2006.01)

(52) U.S. Cl.
  CPC ............ *C07F 9/4875* (2013.01); *C07F 9/4866* (2013.01); *C07F 9/5728* (2013.01); *C07F 9/3276* (2013.01)
  USPC .......................................... 558/110; 558/177

(58) Field of Classification Search
  USPC ................................................ 558/110, 177
  See application file for complete search history.

(56) References Cited

U.S. PATENT DOCUMENTS

| 2008/0255391 A1 | 10/2008 | Gilheany et al. |
| 2010/0099875 A1 | 4/2010 | Stephan et al. |
| 2010/0174079 A1 | 7/2010 | Han et al. |

FOREIGN PATENT DOCUMENTS

JP     2011162503 A     8/2011

OTHER PUBLICATIONS

Qing Xu, et al., "Stereospecific Nucleophilic Substitution of Optically Pure H-Phosphinates: A General Way for the Preparation of Chiral P-Stereogenic Phosphine Oxides," Journal of the American Chemical Society, vol. 130, No. 38, 8 pages, copyright 2008.

Gatineau, et al., "Bulky Optically Active P-Stereogenic Phosphine—Boranes from Pure H-Menthylphosphinates," Journal of the American Chemical Society, 4 pages, 2011.

Yongbo Zhou et al., Stereospecific Halogenation of P(O)—H Bonds with Copper(II) Chloride Affording Optically Active Z1, Z2P(O)Cl; J. Org. Chem. vol. 75, No. 22, 2010, 4 pages.

M.J. Johansson et al., "Recent Advances in the Synthesis of P(III)-Chirogenic Compounds," Dept. of Chemistry and Bioscience, Chalmers University of Technology, copyright 2004 Bentham Science Publications, Ltd., 16 pages.

Arnald Grabulosa et al., "Preparation of Optically Pure P-Stereogenic Trivalent Phosphorus Compounds," ScienceDirect, Coordination Chemistry Reviews 251 (2007) 25-90, Elsevier, 67 pages; www.sciencedirect.com.

K. Michal Pietrusiewicz et al., "Preparation of Scalemic P-Chiral Phophinates and Their Derivatives," Chem. Rev. 1994, 1374-1411, 37 pages copyright 1994 American Chemical Society.

Oleg I. Kolodiazhnyi, "Recent Developments in the Asymmetric Synthesis of P-Chiral Phosphorous Compounds", Elsevier, Tetrahedron: Asymmetry Report No. 140, 46 pages, copyright 2012, www.elsevier.com/locate/tetasy.

*Primary Examiner* — Kristin Vajda
(74) *Attorney, Agent, or Firm* — Charles D. Gunter, Jr.

(57) ABSTRACT

Shown is the preparation and subsequent elaboration of P-chiral compounds that can be used as a building block for many P-chiral ligands used, for example, in asymmetric catalytic reactions. Specifically, a synthesis is shown for RP(O)(OR*)CH$_2$OH, with R=H, Ph, aryl, alkyl, and R*=menthol (and other chiral alcohol-derived moieties), especially HP(O)(OMen)CH$_2$OH (Men=L-menthol). This versatile building block is easily synthesized via reaction of inexpensive starting materials, H$_3$PO$_2$, menthol as the chiral auxiliary, and paraformaldehyde.

11 Claims, No Drawings

SYTHESIS OF P-CHIRAL COMPOUNDS

CROSS REFERENCE TO RELATED APPLICATIONS

This application claims priority from an earlier filed provisional application Ser. No. 61/657,944, filed Jun. 11, 2012, entitled "Synthesis of P-Chiral Compounds," by the same inventors.

ACKNOWLEDGEMENT OF GOVERNMENT SUPPORT

This invention was made partly with Government support under contract 0953368 awarded by the National Science Foundation. The Government has certain rights in this invention.

BACKGROUND OF THE INVENTION

1. Field of the Invention

The present invention relates to a process for the simple and inexpensive preparation of optically active phosphorus (P-chiral) building blocks based on (−)-menthol as the chiral auxiliary. The P-chiral building blocks can be elaborated in many ways through known as well as novel reactions, for example, the stereospecific cleavage of the P(O)CH$_2$OH motif through oxidation.

2. Description of the Prior Art

Molecular chirality plays an important role in a variety of industrial processes. Many chiral and enantiometrically pure compounds are widely used in the preparation of pharmaceuticals, cosmetics, flavors and agricultural chemicals, to name several common uses. Manufacturers of such compounds are often challenged to produce the desired enantiomer in both high yield and purity. There are several approaches to achieve these goals, including effective, but often wasteful, separations and resolutions of the desired compound or through asymmetric catalysis via the creation of chiral centers through complex chiral auxiliaries that are difficult to prepare.

The most common P-chiral compound is PhP(O)(OMen)H. This compound was first described by Mislow in the early 1970's (Farnham, W. B.; Murray, R. K.; Mislow, K. *J. Am. Chem. Soc.* 1970, 92, 5808). The compound was used extensively much later on by Han and coworkers (see *J. Am. Chem. Soc.* 2008, 130, 12648-12655, and references cited therein). Although the latter paper claims a modified preparation, the authors do not report any yield and purify the compound twice by crystallization at −30° C. Clearly, the preparation is inconvenient, expensive, and only applicable to one diastereoisomer of PhP(O)(OMen)H.

At the present time, asymmetric catalysis has proved to be the most effective method to prepare both naturally occurring and synthetic chiral compounds in large quantities. Among the most important compounds utilized for asymmetric catalysis reactions are so-called "P-chiral" ligands. Typically, these phosphine ligands have chirality in the carbon chain (C-chiral) and the phosphorous atom is symmetrical with two identical substituents RP(R$^1$)$_2$. Chirality at the phosphorous (P-chiral) remains the most desirable because the phosphorous is in direct contact with the metal that is actually involved in the catalysis. More selective and efficient catalysis can be attained through this proximity. To date, only a limited number of P-chiral compounds have been reported in the literature.

Because the preparation of P-chiral compounds is truly a "Holy Grail" of organophosphorus chemistry, many relevant works could be mentioned. The following reviews are exemplary of the present state of the art:
1) Grabulosa, A.; Granell, J.; Muller, G. *Coord. Chem.* 2007, 251, 25-90.
2) Johansson, M. J.; Kann, N. C. *Mini Rev. Org. Chem.* 2004, 1, 233-247.
3) Pietrusiewicz, K. M.; Zablocka, M. *Chem. Rev.* 1994, 94, 1375-1411.

SUMMARY OF THE INVENTION

The synthesis of P-chiral compounds is important to many applications, especially in the preparation of phosphine ligands for asymmetric catalysis (impacting both the synthesis of "fine" chemicals and industrial intermediates). As has been briefly mentioned, the vast majority of chiral phosphine ligands have chirality in the carbon chain, whereas the phosphorus atom is symmetrical with two identical substituents RP(R$^1$)$_2$ (such as R$^1$=Ph, i-Pr, t-Bu, etc.). Yet, chirality at phosphorus is most desirable because it is directly in contact with the metal actually involved in the catalysis. Perhaps the best known example of a P-chiral ligand is diPAMP [(R,R)-1,2-Bis[(2-methoxyphenyl)(phenylphosphino)]ethane, currently selling for about $ 77.70 for 100 mg from a commercially available source.

The present invention concerns the preparation (and subsequent elaboration) of RP(O)(OR*)CH$_2$OH, with R=H, Ph, alkyl, aryl, cinnamyl, etc; and R*=menthyl (and other chiral alcohol-derived moieties), especially HP(O)(OMen)CH$_2$OH (where Men is menthol). Most preferably, R is independently selectable from among H and Ph and R* is L-menthol. This versatile building block is easily synthesized via the reaction of inexpensive starting materials, H$_3$PO$_2$, menthol and para-formaldehyde. The compound is easily crystallized at room temperature or in a simple freezer. From this starting compound, virtually any final product can be prepared with on the crystallization step being required as the source of chirality.

The invention offers a number of advantages, including the following, among others:

The power of the invention is multifold: 1) menthol is very inexpensive, 2) HP(O)(OMen)CH$_2$OH is a very versatile building block, 3) the synthesis is inexpensive, for example, involving H$_3$PO$_2$, menthol, para-formaldehyde), 4) the compound can be crystallized very easily at room temperature or −18° C. (actually a simple freezer), in two cases to be described, 5) the method does not rely on any PCl-containing reagent, 6) large quantities can be prepared, and 6) virtually any final product can be prepared with only the initial crystallization step required as the source of chirality. This avoids tedious resolutions or crystallizations near the end of a multiple-step synthesis. L-Menthol is probably the most inexpensive alcohol available ($ 129 for 1 kg, or $1,000 for 25 kg from Sigma-Aldrich at the present time); and the enantiomer is also available, although much more expensive ($ 184 for 50 g). However, this enantiomer is not necessary for the practice of the present invention.

While the chemical yield for the preparation of highly optically-enriched HP(O)(OMen)CH$_2$OH has not been completely optimized, a routine 10% yield can be obtained at present, and improvements are being examined in keeping with the principles of the invention, described more fully in the Detailed Description which follows. Because of the inexpensive and simple nature of the reaction, nothing remotely close has been found by Applicants to exist in the literature.

Although not absolutely required, another aspect of the invention is the stereospecific cleavage of the P(O)CH$_2$OH moiety via oxidative cleavage. Methods for the oxidation of alcohols to aldehydes are available, and especially either "Swern oxidation (DMSO/oxalyl chloride)" and "Corey-Kim oxidation (Me$_2$S/N-chlorosuccinimide)" are most appropriate. Although various P—H protecting groups have been reported, to the best of Applicant's knowledge, none involve P(O)CH$_2$OH under oxidative conditions.

Whereas various methods have been reported for the preparation of specific P-chiral building blocks, based on kinetic resolution, or on chiral auxiliaries, typically these have severe limitation in the scope of their application. More than 40 years ago, Mislow and others pioneered the field of P-chiral compounds and the study of their reactivities. A case in point is menthyl phenyl-H-phosphinates PhP(O)(OMen)H 1, which have since been employed in various reactions such as cross-coupling substitution, or hydrophosphinylation. How-

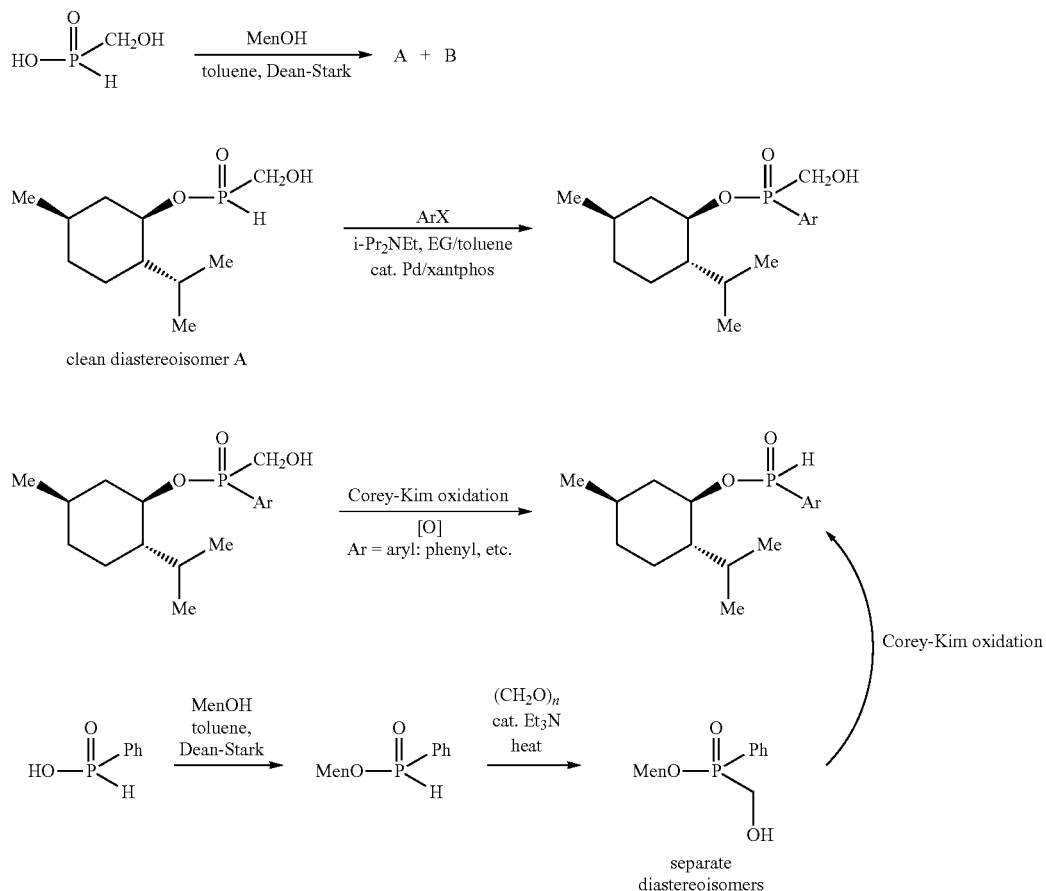

Additional objects, features and advantages will be apparent in the written description which follows.

DETAILED DESCRIPTION OF THE INVENTION

The preferred version of the invention presented in the following written description and the various features and advantageous details thereof are explained more fully with reference to the non-limiting examples and as detailed in the description which follows. Descriptions of well-known components and processes and manufacturing techniques are omitted so as to not unnecessarily obscure the principle features of the invention as described herein. The examples used in the description which follows are intended merely to facilitate an understanding of ways in which the invention may be practiced and to further enable those skilled in the art to practice the invention. Accordingly, the examples should not be construed as limiting the scope of the claimed invention.

As has been briefly discussed, preparing P-chiral compounds remains a frontier in organophosphorus chemistry.

ever, enriched diastereoisomers of 1 remain difficult to prepare as the isolation requires low-temperature recrystallization (multiple crystallizations below −30° C. or −70° C.). Analogous chemistry (PhPCl$_2$+R*OH or R*OPCl$_2$) has been reported recently using other chiral alcohols. In the final analysis, these methods still require cumbersome crystallization procedures and are limited in terms of the phosphorus compounds that are accessible and therefore the final products that can be derived from them.

In one aspect, Applicants have discovered a novel P-chiral building block useful in the preparation of a variety of P-chiral organophosphorus compounds without using halogenated phosphorus starting materials, the building block having the formula:

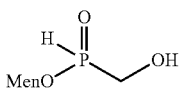

wherein the P-chiral building block is made from -(−) menthol as a starting material.

In another aspect of the invention, the P-chiral building block can take the form:

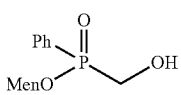

wherein the P-chiral building block is made from -(−)-menthol as a starting material.

In one preferred form, the building blocks so produced are used to produce compounds of the formula:

RP(O)(OR*)CH₂OH where R=H, Ph, aryl, alkyl, cinnamyl and R*=menthol or derived from any other chiral alcohol.

The starting blocks of the invention can be used to make a P-chiral compound of the formula:

RP(O)(OR*)CH₂OH where R=H, Ph, aryl, alkyl, cinnamyl and R*=menthyl or derived from any other chiral alcohol;
wherein the compound is made from a starting material having the formula:

the starting material being crystallized at about −18° C.

In another aspect of the invention, the building blocks are used to produce a P-chiral compound of the formula:

RP(O)(OR*)CH₂OH where R=H, Ph, aryl, alkyl, cinnamyl and R*=menthol or derived from any other chiral alcohol;
wherein the compound is made from a starting material having the formula:

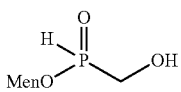

the starting material being crystallized at room temperature.

A process is also shown for the synthesis of asymmetric non-racemic P-chiral compound of the formula:

RP(O)(OR*)CH₂OH where R=H, Ph, aryl, alkyl, cinnamyl and R*=menthol;
wherein the P-chiral compound is made by reacting (−)-menthol, H₃PO₂ and paraformaldehyde as reactants, followed by crystallization between room temperature and about −18° C. to produce a given yield for the process.

The process is characterized by the absence of halogenated phosphorus starting materials. Unlike the prior art processes, the P-chiral starting blocks are crystallized at room temperature or in a simple freezer. In another aspect of the process, the initial reactants make up a mother liquor, and wherein the yield of the process is improved by cross-coupling the mother liquor followed by crystallization.

Other candidate chiral alcohols include: (1R)-endo-(+)-fenchy alcohol; (−)-borneol; and D-(−)-pantolactone.

However, for preparing the chiral building blocks, in the most preferred aspects, R=H and R*=CH₂OH or R=Ph and R*=CH₂OH.

Thus, in one aspect, the present invention involves the description of an extremely simple approach for the preparation of two versatile P-chiral building blocks, easily produced inexpensively on a multigram scale, and without the need for RPCl₂ precursors. These intermediates also allow much more flexibility for their functionalization into useful P-chiral compounds. The two building blocks 2 and 3 are crystallized in high (>95%) diastereoisomeric purities at −18° C. (in a regular freezer) in the case of 2, or at room temperature in the case of 3, respectively.

(R$_p$)

(S$_p$)

Compound 2 is prepared from hypophosphorous acid, paraformaldehyde and (−)-menthol in 9% yield (>6 g), and compound 3 is prepared from phenyl-H-phosphinic acid, (−)-menthol, and paraformaldehyde in 26% yield (>16 g) (Scheme 1). While the isolated yields are low, these still compare to literature methods and multigrams quantities are available in a single preparation. The structures of the diastereoisomers were determined by single X-ray crystallography (FIG. 1).

Scheme 1. Preparation of compounds 2 and 3.

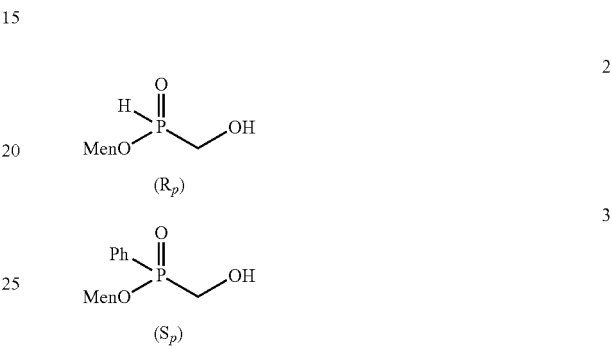

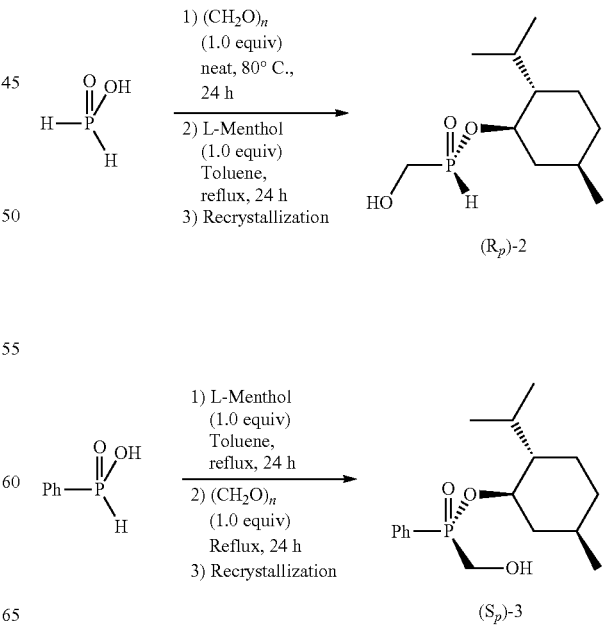

FIG. 1. Single X-ray crystal structures of 2 and 3.

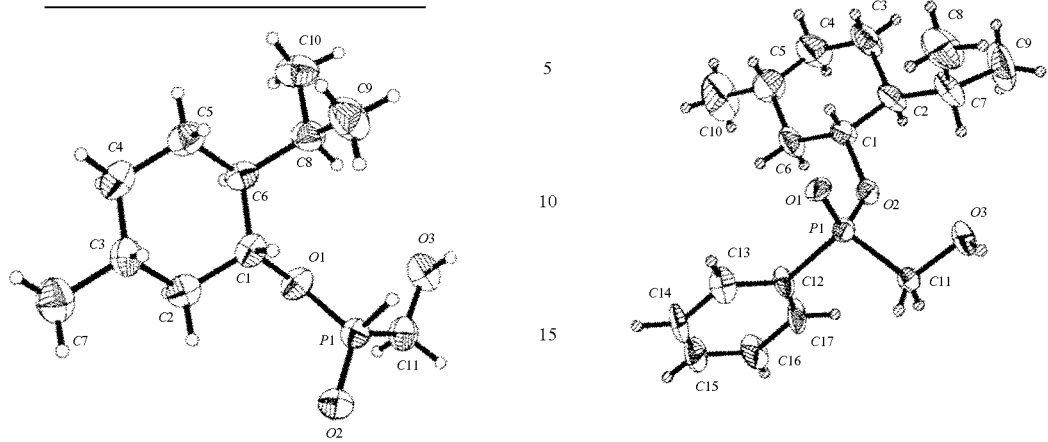

Scheme 2. Functionalization of the P-chiral hydroxymethyl compounds.

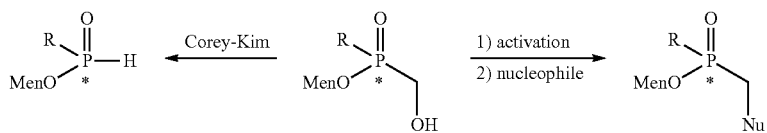

The hydroxymethyl handle also provides a way to functionalize these P-chiral building blocks (Scheme 2). We recently reported the Corey-Kim oxidation of (hydroxymethyl)phosphinates into the corresponding H-phosphinates. Thus, compound 2 can be viewed as a protected chiral equivalent of alkyl phosphinates ROP(O)H$_2$, since it can be stereospecifically alkylated to form 4, or cross-coupled to form 5 (Scheme 3).

Scheme 3. Functionalization of 2 and 3, and stereodivergent synthesis of PhP(O)(OMen)H 1.

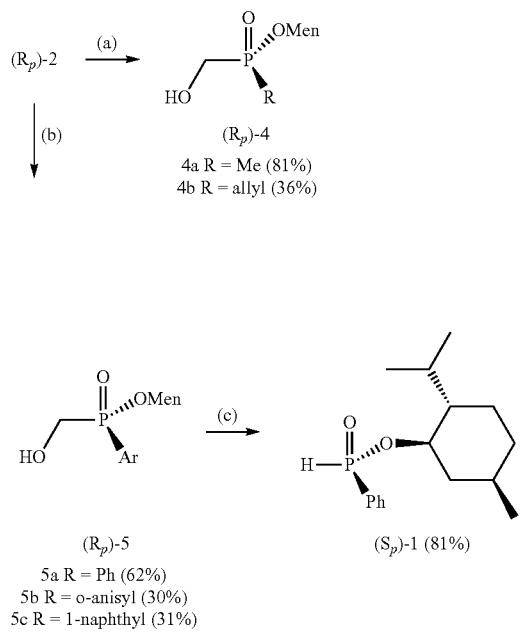

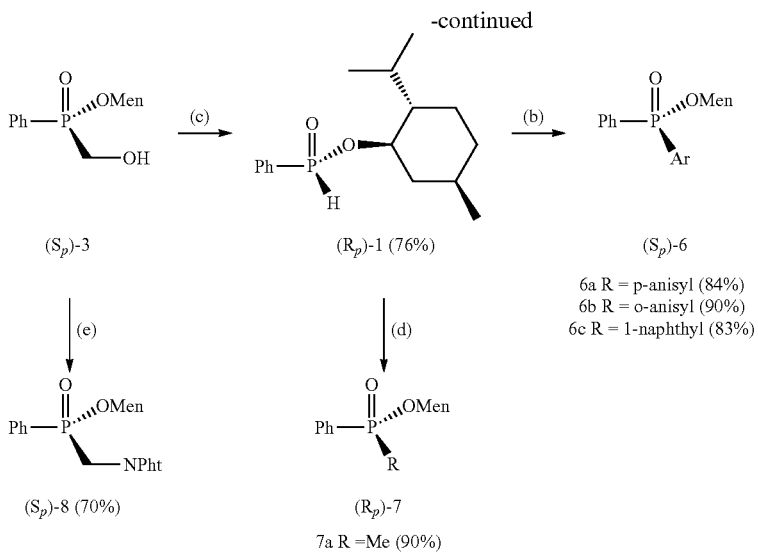

i) LiHMDS (2 equiv), THF, -78° C., 15 min; ii) MeI or allylBr (1 equiv), -78° C., 3 h. (b) ArBr (1 equiv), Pd(OAc)$_2$ (2 mol %), xantphos (2.2 mol %), i-Pr$_2$NEt (1.3 equiv), toluene/ethylene glycol (9:1, v/v), 115° C., 24 h. (c) i) N-chlorosuccinimide (1.5 equiv), Me$_2$S (1.5 equiv), CH$_2$Cl$_2$, -78° C., 10 min. ii) 3 or 5a (1 equiv), -78° C., 1 h. iii) Et$_3$N (5 equiv), -78° C. to rt, 1 h. (d) i) BSA (2 equiv), CH$_2$Cl$_2$; ii) MeI (2 equiv), 0° C., 2 h; or allylBr (2 equiv), rt, 4 days (e) phthalimide (1.3 equiv), PyPPh$_2$ (1.3 equiv), DIAD (1.3 equiv), CH$_2$Cl$_2$, rt, 24 h.

For example, cross-coupling of 2 with bromobenzene gives (R$_P$)-5a (=(R$_P$)-3) in 62% yield, and subsequent oxidative cleavage delivers (S$_P$)-1 in 81% yield. Compound 3 can be oxidized to form (R$_P$)-1 stereospecifically, in 76% yield. Therefore, cross-coupling/oxidation of 2 leads to the stereocomplementary isomer obtained by the direct oxidation of 3, so that either diastereoisomer of 1 is easily obtained using inexpensive (−)-menthol in both cases. Because of the ease of obtaining 2 and 3, and then 1 this approach is competitive with the direct but complicated synthesis of 1 from PhPCl$_2$ or MenOPCl$_2$. Furthermore, these literature syntheses of the (S$_P$) stereoisomer require the use of expensive D-(+)-menthol. The usefulness of compound 1 in asymmetric organophosphorus synthesis is well-established. However, it is obviously limited to phenyl-containing products. Therefore the novel building block 2 offers much flexibility previously unavailable. Also, the presence of the hydroxymethyl group in both 2 and 3 provides further opportunities for functionalization since the carbon can be preserved if desired.

Another example of exploitation of the CH$_2$OH moiety is the [2,3]-Wittig rearrangement (Scheme 4). Compound 3 is allylated to intermediate 9. Subsequent treatment of 9 with s-BuLi delivers the rearranged products 10. In all instances, a single diastereoisomer is obtained. At this time, the configuration of the stereocenters in the side-chain has not been assigned.

Scheme 4. [2,3]-Wittig rearrangement of 3.

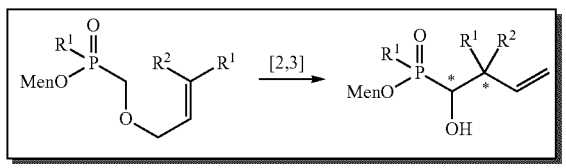

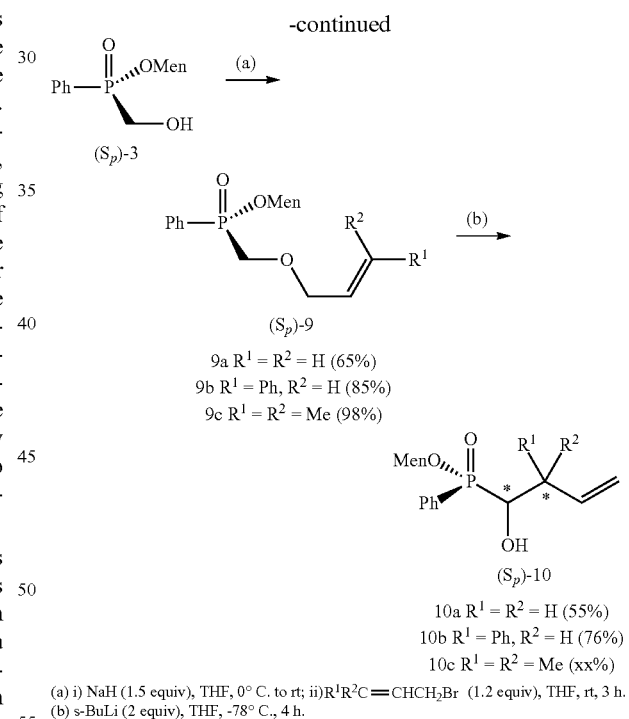

(a) i) NaH (1.5 equiv), THF, 0° C. to rt; ii)R$^1$R$^2$C=CHCH$_2$Br (1.2 equiv), THF, rt, 3 h. (b) s-BuLi (2 equiv), THF, -78° C., 4 h.

The preparation of a variety of P-chiral organophosphorus compounds from 1 (secondary and tertiary phosphine oxides) and from other menthyl esters is well-known in the literature (Scheme 5). For example, displacement of menthyl H-phosphinates with organometallic reagents gives the corresponding secondary phosphine oxide stereoselectively (inversion). Similarly, disubstituted menthyl phosphinates are also displaced with inversion of configuration. Finally, several methods are available to convert tertiary phosphine oxides into the corresponding P-chiral phosphine (or its borane complex) through either retention or inversion of configuration.

Scheme 5. Elaboration of menthyl phosphinates

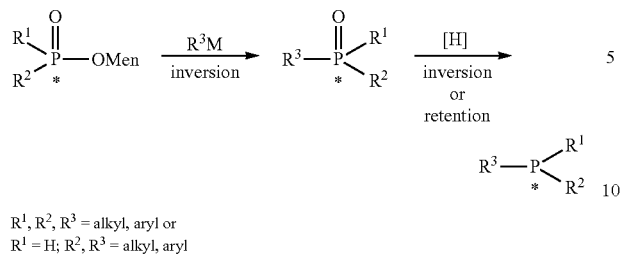

$R^1, R^2, R^3$ = alkyl, aryl or
$R^1$ = H; $R^2, R^3$ = alkyl, aryl

Initial Experimental Work: Procedures for the Menthyl Derivatives:

The following section will detail the procedures initially used to prepare several menthyl derivatives of the type under consideration.

General Chemistry:

$^1$H NMR spectra were recorded on a 300-MHz spectrometer. Chemical shift for $^1$H NMR spectra (in parts per million) relative to internal tetramethylsilane (Me$_4$Si, δ=0.00 ppm) with CDCl$_3$. $^{13}$C NMR spectra were recorded at 75 MHz. Chemical shifts for C NMR spectra are reported (in parts per million) relative to CDCl$_3$ (δ=77.0 ppm). $^{31}$P NMR spectra were recorded at 121 MHz, and chemical shifts reported (in parts per million) relative to external 85% phosphoric acid (δ=0.0 ppm). TLC plates were visualized by UV or immersion in anisaldehyde stain (by volume: 93% ethanol, 3.5% sulfuric acid, 1% acetic acid, and 2.5% anisaldehyde) followed by heating.

Reagent and Solvents:

All starting materials were purchased from commercial sources and used as received. The solvents were distilled under N$_2$ and dried according to standard procedures (THF from Na/benzophenone ketyl; DMF from MgSO$_4$; CH$_3$CN, toluene and dichloromethane from CaH$_2$).

$^{31}$P NMR Yield Measurements:

The NMR yields are determined by integration of all the resonances in the $^{31}$P spectra, an approach which is valid if no phosphorus-containing gas (i.e. PH$_3$) evolves, or if the precipitate in a heterogeneous mixture does not contain phosphorus. The yields determined by NMR are generally accurate within ~10% of the value indicated, and are reproducible.

L-menthyl(hydroxymethyl)phenyl-($S_p$)phosphinate
(3)

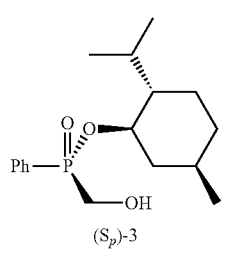

($S_p$)-3

In a flask equipped with a Dean-Stark trap were introduced phenyl-H-phosphinic acid (28.99 g, 204 mmol, 1.02 equiv), L-menthol (31.25 g, 200 mmol, 1.0 equiv) and toluene (200 mL). After 24 h at reflux under N$_2$, the reaction was cooled down to rt. Paraformaldehyde (6.61 g, 200 mmol, 1.0 equiv) was added and the reaction was stirred for 24 h at reflux. The solvent was evaporated and the residue was dissolved into Et$_2$O (100 mL). Hexanes (200 mL) were then added. The solution was then left at rt to allow the slow recrystallization of the desired compound as a white crystals (16.1 g, 26%, de>95%). $^{31}$P NMR (121.47 MHz, CDCl$_3$): δ=37.2 (s); $^1$H NMR (300 MHz, CDCl$_3$): δ=7.77-7.87 (m, 2H), 7.52-7.60 (m, 1H), 7.42-7.51 (m, 2H), 4.29-4.43 (m, 2H), 3.93-4.10 (m, 2H), 2.26 (dquint., J=2.6 and 7.0 Hz, 1H), 1.80-1.91 (m, 1H), 1.57-1.73 (m, 2H), 1.26-1.47 (m, 2H), 0.96 (d, J=7.1 Hz, 3H), 0.74-1.13 (m, 3H), 0.89 (d, J=7.0 Hz, 3H), 0.78 (d, J=6.4 Hz, 3H); $^{13}$C NMR (75.46 MHz, CDCl$_3$): δ=132.3 (d, $J_{PCCCC}$=2.8 Hz), 131.7 (d, $J_{PCCC}$=9.9 Hz, 2C), 130.6 (d, $J_{PC}$=123 Hz), 128.3 (d, $J_{PCC}$=12.1 Hz, 2C), 77.1 (d, $J_{POC}$=8.3 Hz), 60.2 (d, $J_{PC}$=117 Hz), 48.7 (d, $J_{POCC}$=6.1 Hz), 43.2, 34.0, 31.4, 25.5, 22.8, 21.9, 21.1, 15.7; HRMS (EI+) m/z calcd for C$_{16}$H$_{28}$O$_3$P ([M+H]$^+$) 311.1776. found 311.1766

L-menthyl(hydroxymethyl)-H—($R_p$)phosphinate

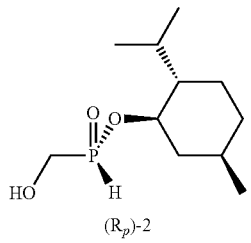

($R_p$)-2

In a round bottom flask were introduced H$_3$PO$_2$ (39.6 mL, 300 mmol, 1.0 equiv, 50% in water) and paraformaldehyde (11.9 g, 360 mmol, 1.2 equiv). The mixture was stirred for 20 h at 80° C. under N$_2$. The reaction was then allowed to cool down to rt. The residue obtained was diluted in toluene (300 mL) and then transferred in a bigger flask equipped with a Dean-Stark trap. L-menthol (46.9 g, 300 mmol, 1.0 equiv) was added and the reaction was stirred for 24 h at reflux. The solvent was then evaporated and the residue obtained was dissolved into Et$_2$O (100 mL). Hexanes (200 mL) was then added and the solution was left in the freezer (−18° C.) to allow the slow recrystallization of the desired compound as a white crystals (6.33 g, 9%, de>99%). Mp=101-102° C.; $^{31}$P NMR (121.47 MHz, CDCl$_3$): δ=34.9 (dm, J=542 Hz); $^1$H NMR (300 MHz, CDCl$_3$): δ=7.16 (dm, J=542 Hz, 1H), 4.04-4.23 (m, 2H), 3.82-4.00 (m, 2H), 2.14-2.24 (m, 1H), 1.98-2.11 (m, 1H), 2.04 (dquint., J=2.4 and 7.0 Hz, 1H), 1.62-1.73 (m, 2H), 1.34-1.52 (m, 2H), 1.24 (q, J=12.0 Hz, 1H), 0.93 (d, J=6.7 Hz, 6H), 0.76-1.10 (m, 2H), 0.80 (d, J=7.0 Hz, 3H); $^{13}$C NMR (75.46 MHz, CDCl$_3$): δ=79.3 (d, $J_{POC}$=8.3 Hz), 59.7 (d, $J_{PC}$=111 Hz), 48.5 (d, $J_{POCC}$=5.5 Hz), 43.3, 33.8, 31.5, 25.6, 22.9, 21.8, 20.8, 15.7; [α]$_D$=−61.37°

L-menthyl(hydroxymethyl)phenyl ($R_p$)phosphinate

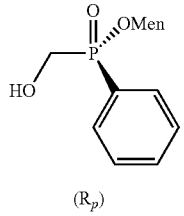

($R_p$)

In a tube for multisynthetizer were introduced L-menthyl (hydroxymethyl)-H—($R_p$)phosphinate (234.3 mg, 1.0 mmol, 1.0 equiv), Pd(OAc)$_2$ (4.5 mg, 0.02 mmol, 2 mol %) and Xantphos (12.7 mg, 0.022 mmol, 2.2 mol %). The tube was placed under N$_2$. Toluene (4.5 mL) was then added followed by ethylene glycol (0.5 mL), DIPEA (0.23 mL, 1.3 mmol, 1.3 equiv) and bromobenzene (0.11 mL, 1.0 mmol, 1.0 equiv). After 24 h at reflux, the reaction was allowed to cool down to rt. Ethanol was then added to allow us to do $^{31}$PNMR by forming a homogeneous mixture. After removing the solvents under vacuum, EtOAc was added and the organic layer was washed with NaHCO$_3$ and brine, dried over MgSO$_4$, filtered and concentrated. The residue obtained was purified by column chromatography (Hexanes/EtOAc 7:3) to afford the product as a white solid (192 mg, 62%, de>99%). $^{31}$P NMR (121.47 MHz, CDCl$_3$): δ=37.4 (s); $^1$H NMR (300 MHz, CDCl$_3$): δ=7.80-7.91 (m, 2H), 7.45-7.62 (m, 3H), 4.09-4.21 (m, 1H), 4.02-4.08 (m, 2H), 2.77-2.87 (m, 1H), 2.29-2.39 (m, 1H), 1.90-2.05 (m, 1H), 1.58-1.69 (m, 3H), 1.22-1.50 (m, 2H), 0.93 (d, J=6.2 Hz, 3H), 0.85 (d, J=7.0 Hz, 3H), 0.76-1.02 (m, 2H), 0.47 (d, J=7.0 Hz, 3H); $^{13}$C NMR (75.46 MHz, CDCl$_3$): δ=132.3 (d, $J_{PCCCC}$=2.7 Hz), 131.8 (d, $J_{PCCC}$=9.9 Hz, 2C), 129.4 (d, $J_{PC}$=124 Hz), 128.4 (d, $J_{PCC}$=12.1 Hz, 2C), 77.4 (d, $J_{POC}$=8.3 Hz), 60.4 (d, $J_{PC}$=115 Hz), 48.6 (d, $J_{POCC}$=6.0 Hz), 43.6, 34.0, 31.5, 25.4, 22.6, 22.0, 21.0, 15.2; HRMS (EI+) m/z calcd for C$_{17}$H$_{27}$O$_3$P ([M+H]$^+$) 311.1776. found 311.1773

L-menthyl phenyl-H—($R_p$)phosphinate

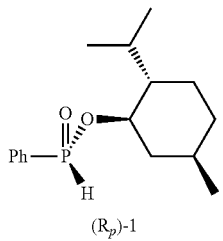 [SMILES: CC(C)[C@@H]1CC[C@@H](C)C[C@H]1O[P@@H](=O)c1ccccc1]

($R_p$)-1

To a solution of N-chlorosuccinimide (1.0 g, 7.5 mmol, 1.5 equiv) in dichloromethane (80 mL) at −78° C. and under N$_2$ was added dropwise a solution of dimethyl sulfide (0.55 mL, 7.5 mmol, 1.5 equiv) in dichloromethane (10 mL). After 10 minutes at −78° C., a solution of L-menthyl(hydroxymethyl) phenyl ($S_p$)phosphinate 3 (1.55 g, 5.0 mmol, 1.0 equiv) in dichloromethane (10 mL) was added over 20 minutes. After 1 h at −78° C., triethylamine (3.48 mL, 25.0 mmol, 5.0 equiv) was added over 15 minutes and the reaction was allowed to warm to rt. After 1 h at rt, water was added and the two layers were separated. The aqueous layer was then washed with dichloromethane (2×). The combined organic layer was dried over MgSO$_4$, filtered and concentrated under vacuum. The residue obtained was dissolved into EtOAc and washed with brine. The combined organic layer was dried over MgSO$_4$, filtered and concentrated under vacuum. The residue obtained was purified by column chromatography (Hexanes/CH$_2$Cl$_2$ 5:5 to 0:10) to afford the product as a colorless oil (1.07 g, 76%, de>99%). $^{31}$P NMR (121.47 MHz, CDCl$_3$): δ=24.7 (dm, J=553 Hz); $^1$H NMR (300 MHz, CDCl$_3$): δ=7.73-7.84 (m, 2H), 7.66 (d, J=553 Hz, 1H), 7.46-7.64 (m, 3H), 4.22-4.36 (m, 1H), 2.14-2.27 (m, 2H), 1.62-1.75 (m, 2H), 1.38-1.54 (m, 2H), 1.24 (q, J=11.2 Hz, 1H), 0.78-1.13 (m, 2H), 0.96 (d, J=7.0 Hz, 3H), 0.90 (d, J=6.4 Hz, 3H), 0.86 (d, J=7.0 Hz, 3H)

L-menthyl(o-anisole)phenyl-H—($S_p$)phosphinate

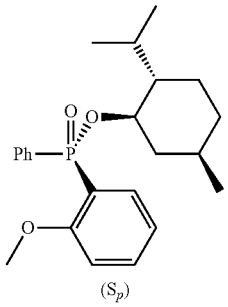 [SMILES: COc1ccccc1[P@@](=O)(O[C@@H]1C[C@H](C)CC[C@H]1C(C)C)c1ccccc1]

($S_p$)

In a tube for multisynthetizer were introduced L-menthyl phenyl-H—($R_p$)phosphinate (280.3 mg, 1.0 mmol, 1.0 equiv), Pd(OAc)$_2$ (4.5 mg, 0.02 mmol, 2 mol %) and Xantphos (12.7 mg, 0.022 mmol, 2.2 mol %). The tube was placed under N$_2$. Toluene (4.5 mL) was then added followed by ethylene glycol (0.5 mL), DIPEA (0.23 mL, 1.3 mmol, 1.3 equiv) and 2-bromoanisole (0.13 mL, 1.0 mmol, 1.0 equiv). After 24 h at reflux, the reaction was allowed to cool down to rt. Ethanol was then added to allow us to do $^{31}$PNMR by forming a homogeneous mixture. After removing the solvents under vacuum, EtOAc was added and the organic layer was washed with NaHCO3 and brine, dried over MgSO$_4$, filtered and concentrated. The residue obtained was purified by column chromatography (Hexanes/EtOAc 9:1 to 8:2) to afford the product as a yellow oil (347 mg, 90%, de>99%). $^{31}$P NMR (121.47 MHz, CDCl$_3$): δ=27.6 (s); $^1$H NMR (300 MHz, CDCl$_3$): δ=7.99-8.11 (m, 1H), 7.76-7.88 (m, 2H), 7.35-7.54 (m, 4H), 7.02-7.11 (m, 1H), 6.77-6.86 (m, 1H), 4.15-4.28 (m, 1H), 3.61 (s, 3H), 2.10-2.25 (m, 2H), 1.56-1.71 (m, 2H), 1.30-1.51 (m, 2H), 1.21 (q, J=11.2 Hz, 1H), 0.78-1.03 (m, 2H), 0.87 (d, J=7.1 Hz, 3H), 0.84 (d, J=6.4 Hz, 3H), 0.48 (d, J=6.7 Hz, 3H)

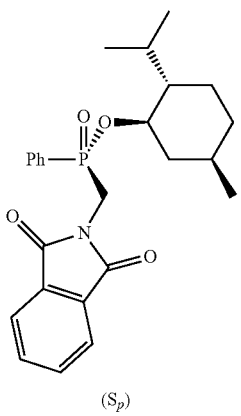 [SMILES: CC(C)[C@@H]1CC[C@@H](C)C[C@H]1O[P@](=O)(CN1C(=O)c2ccccc2C1=O)c1ccccc1]

($S_p$)

L-menthyl(hydroxymethyl)phenyl ($S_p$)phosphinate (620.7 mg, 2.0 mmol, 1.0 equiv), phthalimide (382.5 mg, 2.6 mmol, 1.3 equiv) and diphenyl-2-pyridylphosphine (684.5 mg, 2.6 mmol, 1.3 equiv) were introduced in a flask, placed under N$_2$ and solubilized in CH$_2$Cl$_2$ (20 mL). Diisopropyl azodicarboxylate (0.51 mL, 2.6 mmol, 1.3 equiv) was then added and the reaction was stirred for 24 h at rt. Water and brine (1:1) were added and the two layers were separated. The aqueous layer was then extracted with CH$_2$Cl$_2$ (2×). The combined organic layers was dried over MgSO$_4$, filtered and concentrated under vacuum. The residue obtained was purified by column chromatography (hexanes/EtOAc 9:1 to 7:3) to afford the product as a white solid (612 mg, 70%, de=95%). $^{31}$P NMR (121.47 MHz, CDCl$_3$): δ=31.4 (s); $^1$H NMR (300 MHz, CDCl$_3$): δ=7.79-7.91 (m, 4H), 7.68-7.75 (m, 2H), 7.52-7.60 (m, 1H), 7.42-7.51 (m, 2H), 4.33-4.46 (m, 1H), 4.10-4.30 (m, 2H), 2.17 (dquint., J=2.3 and 6.7 Hz, 1H), 1.78-1.88 (m, 1H), 1.55-1.69 (m, 2H), 1.20-1.46 (m, 2H), 0.94-1.12 (m, 2H), 0.72-0.88 (m, 1H), 0.84 (d, J=7.0 Hz, 3H), 0.79 (d, J=7.0 Hz, 3H), 0.75 (d, J=6.8 Hz, 3H); $^{13}$C NMR (75.46 MHz, CDCl$_3$): δ=166.6 (2C), 134.0 (2C), 132.5 (d, J$_{PCCCC}$=2.8 Hz), 131.7 (2C), 131.6 (d, J$_{PCCC}$=8.8 Hz, 2C), 131.3 (d, J$_{PC}$=130 Hz), 128.3 (d, J$_{PCC}$=12.7 Hz, 2C), 123.2 (2C), 77.6 (d, J$_{POC}$=7.7 Hz), 48.5 (d, J$_{POCC}$=6.1 Hz), 42.9, 38.1 (d, J$_{PC}$=107 Hz), 33.8, 31.3, 25.3, 22.5, 21.8, 20.9, 15.4; HRMS (EI+) m/z calcd for C$_{25}$H$_{31}$NO$_4$P ([M+H]$^+$) 440.1991. found 440.1985

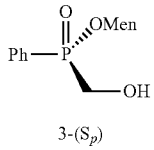

3-(S$_p$)

1) Applicants have not changed the scales for the preparation of 2 and 3, but these multigram scales have been repeated successfully. An additional aspect of the invention was to "recycle" the mother liquor for compound 2. In this process, after the amount of crystals 2 (9% yield, >6 g) have been obtained, Applicants carried out a "cross-coupling" on the mother liquor and crystallizing the product 3-(R$_P$) in 24% yield, at room temperature. Note that the product is stereocomplementary to 3-(S$_p$) which is obtained from PhP(O)(OH)H as described in the previous discussion (26% yield, >16 g). Thus, we have a way to increase the yield of valuable compounds in the preparation of 2.

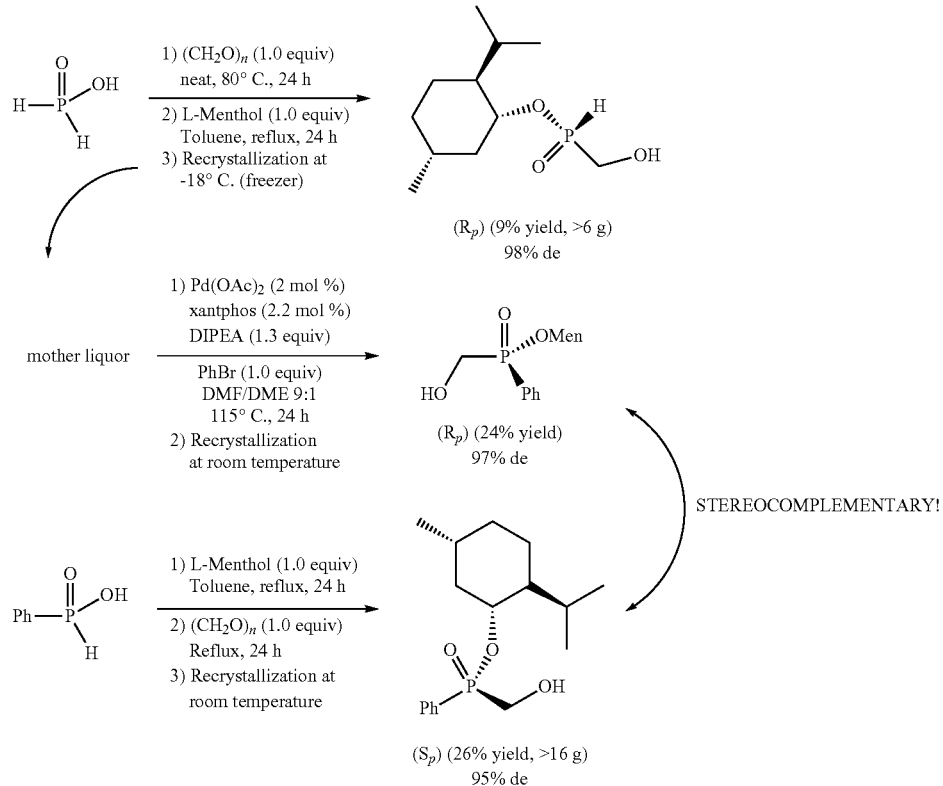

Further Experimental Work:

Since the initial experimental work described above, Applicants have performed additional work which verifies the earlier findings, as well as introducing certain new and novel aspects of the invention. With respect to the initial compounds 2 and 3:

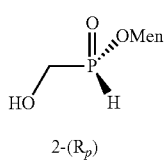

2-(R$_p$)

The stereocomplementarity characteristic is important because it means that either chirality can be made at phosphorus using the same L-menthol (which is the less expensive starting material, the other menthol costing on the order of 50× more). The same stereocomplementarity characteristic also means that is possible to make, for example, PhP(O)(OMen)H with either chirality at phosphorus. This compound has been made before in unreported yield and through difficult crystallizations (see Han and Mislow cited above), and only one chirality can be obtained from L-menthol. This compound has been used to make chiral phosphines as sold, for example, by Katayama Chemical Industries.

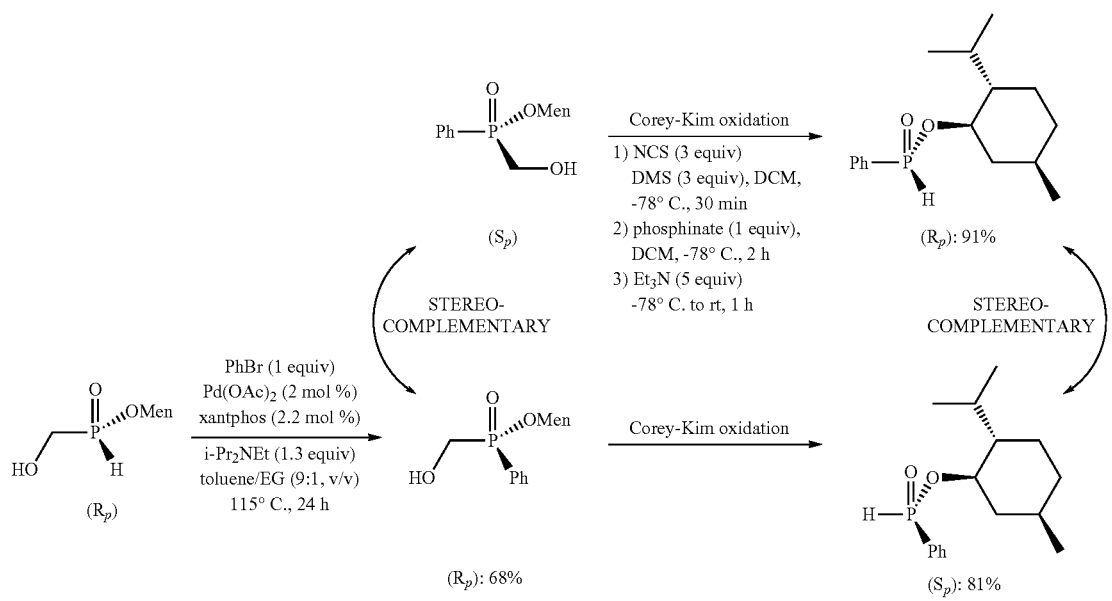

2) In another aspect of the invention, the concept of making RP(O)(OMen)CH$_2$OH was extended to R=cinnamyl, again on multigram scale and with crystallization at room temperature. Cleavage of the CH$_2$OH group was also done.

Transformations of the Building Blocks.

Some of the original transformations in the provisional have been improved in terms of yield, and a few new ones have been added, showing the synthetic flexibility of the compounds.

As mentioned in the literature background, the stereospecific transformation of phosphinates R$^1$R$^2$P(O)(OMen) into chiral phosphines is well precedented in the literature.

Two X-ray crystal structures have been obtained for the Wittig rearrangement.

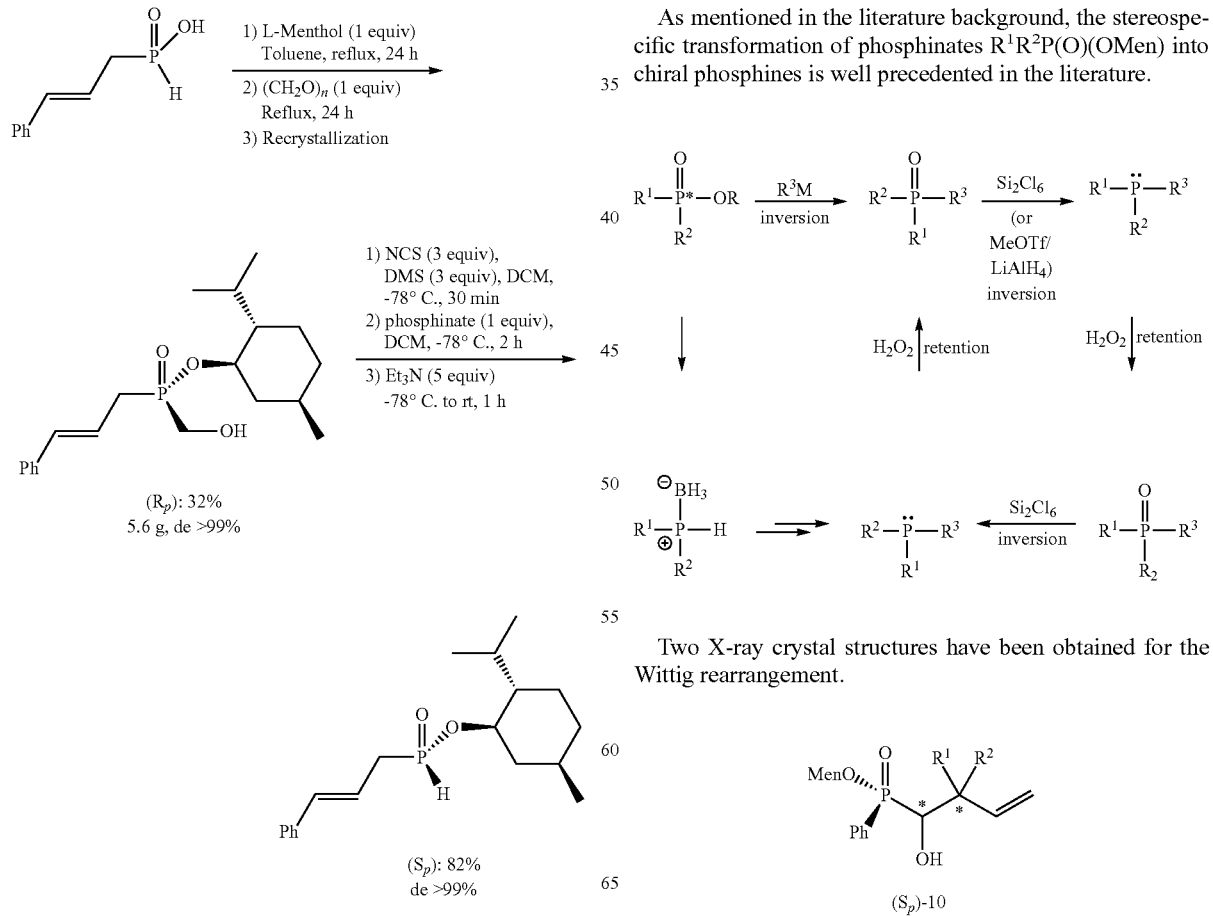

-continued

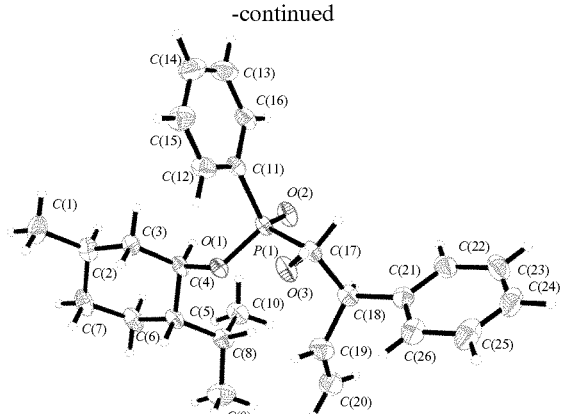

R¹ = Ph, R² = H

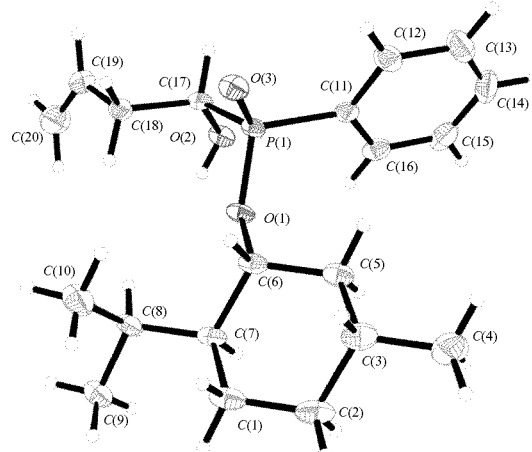

R¹ = R² = H

Further Experimental Examples ($R_p$)-Menthyl(hydroxymethyl)-H-phosphinate 1

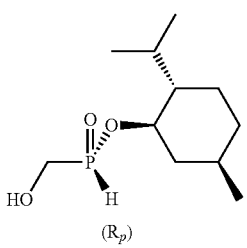

Paraformaldehyde (9.91 g, 330 mmol, 1.1 equiv) and hypophosphorous acid (39.6 g, 300 mmol, 1 equiv, 50% in water) were introduced in a round bottom flask and the reaction mixture was stirred for 20 h at 75° C. The reaction mixture was cooled down to rt and the residue was diluted in toluene (300 mL). L-menthol (46.9 g, 300 mmol, 1 equiv) was added and the reaction mixture was stirred for 24 h at reflux under $N_2$ in a flask equipped with a Dean-Stark trap. The solvent was then removed under vacuum and the residue obtained was dissolved in a mixture of diethyl ether/hexane (50 mL:200 mL) and the flask was placed in the freezer for 2 h (−18° C.). The solid obtained was filtered and solubilized in diethyl ether (200 mL) and placed in the fridge (2° C.) for 3 h to afford the product as white needles (6.33 g, 9%, de=98%). Mp=101-102° C.; $^{31}P$ NMR (121.47 MHz, $CDCl_3$): ☐=−34.9 (dm, J=542 Hz); $^1H$ NMR (300 MHz, $CDCl_3$): ☐=7.16 (dm, J=542 Hz, 1H), 4.04-4.23 (m, 2H), 3.82-4.00 (m, 2H), 2.14-2.24 (m, 1H), 1.98-2.11 (m, 1H), 2.04 (dquint., J=2.4 and 7.0 Hz, 1H), 1.62-1.73 (m, 2H), 1.34-1.52 (m, 2H), 1.24 (q, J=12.0 Hz, 1H), 0.93 (d, J=6.7 Hz, 6H), 0.76-1.10 (m, 2H), 0.80 (d, J=7.0 Hz, 3H); $^{13}C$ NMR (75.46 MHz, $CDCl_3$): ☐☐=79.3 (d, $J_{POC}$=8.3 Hz), 59.7 (d, $J_{PC}$=111 Hz), 48.5 (d, $J_{POCC}$=5.5 Hz), 43.3, 33.8, 31.5, 25.6, 22.9, 21.8, 20.8, 15.7; $[\alpha]_D$=−61.37°

($R_p$)-Menthyl(hydroxymethyl)methylphosphinate 2a

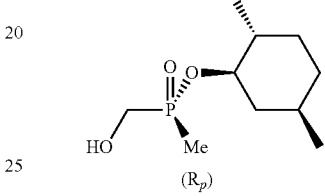

To a solution of 1 (234 mg, 1 mmol, 1 equiv) in dichloromethane (10 mL) at 0° C. and under $N_2$ was added bis(trimethylsilyl)acetamide (0.49 mL, 2 mmol, 2 equiv) followed by iodomethane (0.062 mL, 1 mmol, 1 equiv). The ice-bath was removed and the reaction mixture was then stirred for 20 h at rt. Methanol was added (0.08 mL, 2 mmol, 2 equiv) and the reaction mixture was then concentrated under vacuum. The residue obtained was dissolved in ethyl acetate and the organic layer was washed with a saturated aqueous solution of $NaHCO_3$ and brine. The organic layer was dried over $MgSO_4$, filtered and concentrated under vacuum. The crude obtained was purified by column chromatography (dichloromethane/acetone 10:0 to 7:3) to afford the product as white solid (188 mg, 76%, de>99%). Mp=82-83° C.; $^{31}P$ NMR (121.47 MHz, $CDCl_3$): ☐=51.9 (s); $^1H$ NMR (300 MHz, $CDCl_3$): ☐=4.15-4.28 (m, 1H), 3.73-3.90 (m, 2H), 3.07-3.16 (m, 1H), 2.08-2.18 (m, 1H), 2.06 (dquint., J=2.3 and 7.0 Hz, 1H), 1.62-1.73 (m, 2H), 1.52 (d, J=13.7 Hz, 3H), 1.40-1.58 (m, 1H), 1.24-1.38 (m, 1H), 1.15 (q, J=11.1 Hz, 1H), 0.93 (d, J=6.7 Hz, 3H), 0.91 (d, J=6.7 Hz, 3H), 0.78-1.08 (m, 2H), 0.82 (d, J=6.7 Hz, 3H); $^{13}C$ NMR (75.46 MHz, $CDCl_3$): ☐☐=76.2 (d, $J_{POC}$=7.8 Hz), 60.6 (d, $J_{PC}$=111 Hz), 48.4 (d, $J_{POCC}$=5.5 Hz), 43.4, 33.9, 31.4, 25.6, 22.7, 21.9, 20.9, 15.6, 11.8 (d, $J_{PC}$=91.2 Hz); HRMS (EI+) m/z calcd for $C_{12}H_{26}O_3P$ ([M+H]$^+$) 249.1620. found 249.1621; $[\alpha]_D$=−60.55°

($R_p$)-Menthyl(hydroxymethyl)allylphosphinate 2b

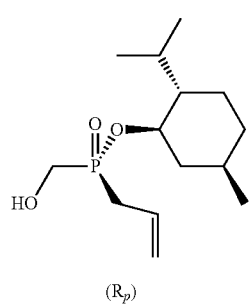 [SMILES: C=CC[P@](=O)(CO)O[C@@H]1C[C@H](C)CC[C@H]1C(C)C]

To a solution of 1 (117 mg, 0.5 mmol, 1 equiv) in dichloromethane (5 mL) at 0° C. and under $N_2$ was added bis(trimethylsilyl)acetamide (0.25 mL, 1 mmol, 2 equiv) followed by allyl bromide (0.09 mL, 1 mmol, 2 equiv). The ice-bath was removed and the reaction mixture was then stirred for 36 h at rt. Methanol was added (0.04 mL, 1 mmol, 2 equiv) and the reaction mixture was then concentrated under vacuum. The residue obtained was dissolved in ethyl acetate and the organic layer was washed with a saturated aqueous solution of $NaHCO_3$ and brine. The organic layer was dried over $MgSO_4$, filtered and concentrated under vacuum. The crude obtained was purified by column chromatography (ethyl acetate/acetone 100:0 to 96:4) to afford the product as white solid (88 mg, 64%, de=95%). Mp=69-71° C.; $^{31}P$ NMR (121.47 MHz, $CDCl_3$): $\delta$=48.4 (s); $^1H$ NMR (300 MHz, $CDCl_3$): $\delta$=5.74-5.93 (m, 1H), 5.19-5.32 (m, 2H), 4.18-4.32 (m, 1H), 3.81-3.89 (m, 2H), 3.53-3.64 (m, 1H), 2.64-2.77 (m, 2H), 2.06-2.18 (m, 2H), 1.61-1.72 (m, 2H), 1.40-1.54 (m, 1H), 1.24-1.39 (m, 1H), 1.15 (q, J=11.5 Hz, 1H), 0.92 (d, J=7.0 Hz, 6H), 0.78-1.08 (m, 2H), 0.81 (d, J=7.0 Hz, 3H); $^{13}C$ NMR (75.46 MHz, $CDCl_3$): $\delta\delta$=127.2 (d, $J_{PCCC}$=9.4 Hz), 120.3 (d, $J_{PCC}$=12.7 Hz), 76.7 (d, $J_{POC}$=8.3 Hz), 59.1 (d, $J_{PC}$=107 Hz), 48.5 (d, $J_{POCC}$=5.5 Hz), 43.4, 34.0, 32.4 (d, $J_{PC}$=86.8 Hz), 31.5, 25.5, 22.7, 22.0, 21.0, 15.6; HRMS (EI+) m/z calcd for $C_{14}H_{27}O_3P$ ([M]$^+$) 274.1698. found 274.1694; $[\alpha]_D$=−71.31°

($R_p$)-Menthyl(hydroxymethyl)phenylphosphinate 3a

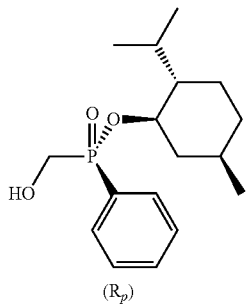 [SMILES: CC(C)[C@@H]1CC[C@@H](C)C[C@H]1O[P@@](=O)(CO)c1ccccc1]

($R_p$)

In a round bottom flask was introduced 1 (117 mg, 0.5 mmol, 1 equiv), $Pd(OAc)_2$ (2.3 mg, 0.01 mmol, 2.0 mol %), xantphos (6.4 mg, 0.011 mmol, 2.2 mol %), a mixture of DMF and 1,2-dimethoxyethane (2.25 mL:0.25 mL), DIPEA (0.11 mL, 0.65 mmol, 1.3 equiv) and bromobenzene (0.05 mL, 0.5 mmol, 1 equiv). The reaction mixture was stirred under a flow of $N_2$ for 10 minutes and then heated at 115° C. for 24 hours before cooling to rt. The solvent was then removed under vacuum and the resulting residue was dissolved in EtOAc and washed with a saturated aqueous solution of $NaHCO_3$ and brine. The organic layer was dried over $MgSO_4$, filtered and concentrated under vacuum. The crude obtained was purified by column chromatography (hexane/ethyl acetate 5:5 to 3:7) to afford the product as a white solid (106 mg, 68%, de=95%). Mp=103-105° C.; $^{31}P$ NMR (121.47 MHz, $CDCl_3$): $\delta$=37.4 (s); $^1H$ NMR (300 MHz, $CDCl_3$): $\delta$=7.80-7.91 (m, 2H), 7.45-7.62 (m, 3H), 4.09-4.21 (m, 1H), 4.02-4.08 (m, 2H), 2.77-2.87 (m, 1H), 2.29-2.39 (m, 1H), 1.90-2.05 (m, 1H), 1.58-1.69 (m, 3H), 1.22-1.50 (m, 2H), 0.93 (d, J=6.2 Hz, 3H), 0.85 (d, J=7.0 Hz, 3H), 0.76-1.02 (m, 2H), 0.47 (d, J=7.0 Hz, 3H); $^{13}C$ NMR (75.46 MHz, $CDCl_3$): $\delta\delta$=132.3 (d, $J_{PCCCC}$=2.7 Hz), 131.8 (d, $J_{PCCC}$=9.9 Hz, 2C), 129.4 (d, $J_{PC}$=124 Hz), 128.4 (d, $J_{PCC}$=12.1 Hz, 2C), 77.4 (d, $J_{POC}$=8.3 Hz), 60.4 (d, $J_{PC}$=115 Hz), 48.6 (d, $J_{POCC}$=6.0 Hz), 43.6, 34.0, 31.5, 25.4, 22.6, 22.0, 21.0, 15.2; HRMS (EI+) m/z calcd for $C_{17}H_{27}O_3P$ ([M+H]$^+$) 311.1776. found 311.1773; $[\alpha]_D$=−69.04°

($R_p$)-Menthyl(hydroxymethyl)p-anisylphosphinate 3b

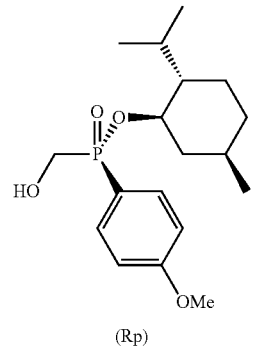 [SMILES: COc1ccc([P@](=O)(CO)O[C@@H]2C[C@H](C)CC[C@H]2C(C)C)cc1]

(Rp)

In a round bottom flask was introduced 1 (117 mg, 0.5 mmol, 1 equiv), $Pd(OAc)_2$ (2.3 mg, 0.01 mmol, 2.0 mol %), xantphos (6.4 mg, 0.011 mmol, 2.2 mol %), a mixture of DMF and 1,2-dimethoxyethane (2.25 mL:0.25 mL), DIPEA (0.11 mL, 0.65 mmol, 1.3 equiv) and 4-bromoanisole (0.06 mL, 0.5 mmol, 1 equiv). The reaction mixture was stirred under a flow of $N_2$ for 10 minutes and then heated at 115° C. for 24 hours before cooling to rt. The solvent was then removed under vacuum and the resulting residue was dissolved in EtOAc and washed with a saturated aqueous solution of $NaHCO_3$ and brine. The organic layer was dried over $MgSO_4$, filtered and concentrated under vacuum. The crude obtained was purified by column chromatography (hexane/ethyl acetate 5:5 to 0:10) to afford the product as a white solid (90 mg, 53%, de=81%). Mp=110-112° C.; $^{31}P$ NMR (121.47 MHz, $CDCl_3$): $\delta$=37.8 (s); $^1H$ NMR (300 MHz, $CDCl_3$): $\delta$=7.74-7.84 (m, 2H), 6.96-7.03 (m, 2H), 4.05-4.18 (m, 1H), 3.96-4.05 (m, 2H), 3.87 (s, 3H), 2.60-2.71 (m, 1H), 2.29-2.39 (m, 1H), 2.01 (dquint., J=2.6 and 7.3 Hz, 1H), 1.58-1.69 (m, 3H), 1.20-1.48 (m, 2H), 0.93 (d, J=6.5 Hz, 3H), 0.87 (d, J=6.7 Hz, 3H), 0.76-1.02 (m, 2H), 0.51 (d, J=6.8 Hz, 3H); $^{13}C$ NMR (75.46 MHz, $CDCl_3$): $\delta\delta$=162.8 (d, $J_{PCCCC}$=2.8 Hz), 133.7 (d, $J_{PCCC}$=11.1 Hz, 2C), 120.5 (d, $J_{PC}$=131 Hz), 114.0 (d, $J_{PCC}$=13.2 Hz, 2C), 77.2 (d, $J_{POC}$=7.7 Hz), 60.5 (d, $J_{PC}$=117 Hz), 55.3, 48.7 (d, $J_{POCC}$=6.0 Hz), 43.6, 34.0, 31.5, 25.4, 22.7, 22.0, 21.0, 15.3; HRMS (EI+) m/z calcd for $C_{18}H_{29}O_4P$ ([M]$^+$) 340.1803. found 340.1801; $[\alpha]_D$=−68.27°

($R_p$)-Menthyl(hydroxymethyl)-1-naphtylphosphinate 3c

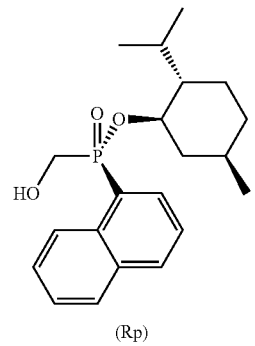 [SMILES: CC(C)[C@@H]1CC[C@@H](C)C[C@H]1O[P@@](=O)(CO)c1cccc2ccccc12]

(Rp)

In a round bottom flask was introduced 1 (117 mg, 0.5 mmol, 1 equiv), Pd(OAc)$_2$ (2.3 mg, 0.01 mmol, 2.0 mol %), xantphos (6.4 mg, 0.011 mmol, 2.2 mol %), a mixture of DMF and 1,2-dimethoxyethane (2.25 mL:0.25 mL), DIPEA (0.11 mL, 0.65 mmol, 1.3 equiv) and 1-bromonaphthalene (0.06 mL, 0.5 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in EtOAc and washed with a saturated aqueous solution of NaHCO$_3$ and brine. The organic layer was dried over MgSO$_4$, filtered and concentrated under vacuum. The crude obtained was purified by column chromatography (hexane/ethyl acetate 5:5 to 0:10) to afford the product as a white solid (152 mg, 84%, de=94%). Mp=102-103° C.; $^{31}$P NMR (121.47 MHz, CDCl$_3$): □=38.6 (s); $^1$H NMR (300 MHz, CDCl$_3$): □=8.54-8.60 (m, 1H), 8.20-8.30 (m, 1H), 8.03-8.10 (m, 1H), 7.88-7.96 (m, 1H), 7.52-7.64 (m, 3H), 4.29-4.43 (m, 1H), 4.08-4.27 (m, 2H), 2.35-2.44 (m, 1H), 1.88-2.00 (m, 1H), 1.59-1.74 (m, 3H), 1.35-1.54 (m, 3H), 0.96 (d, J=6.2 Hz, 3H), 0.84-1.04 (m, 2H), 0.74 (d, J=7.0 Hz, 3H), 0.44 (d, J=6.8 Hz, 3H); $^{13}$C NMR (75.46 MHz, CDCl$_3$): □□=134.3 (d, J$_{PCCC}$=7.7 Hz), 133.6 (d, J$_{PCCC}$=9.4 Hz), 133.5 (d, J$_{PCCCC}$=2.7 Hz), 133.0 (d, J$_{PCC}$=11.6 Hz), 129.0, 127.3, 126.2, 126.2 (d, J$_{PCCC}$=3.3 Hz), 126.1 (d, J$_{PC}$=121 Hz), 124.7 (d, J$_{PCC}$=13.8 Hz), 78.0 (d, J$_{POC}$=8.3 Hz), 61.8 (d, J$_{PC}$=111 Hz), 48.7 (d, J$_{POCC}$=5.0 Hz), 43.6, 34.0, 31.7, 25.4, 22.7, 22.1, 20.9, 15.2; HRMS (EI+) m/z calcd for C$_{21}$H$_{29}$O$_3$P ([M]$^+$) 360.1854. found 360.1860; [α]$_D$=−52.26°

(S$_p$)-Menthyl phenyl-H-phosphinate 4a

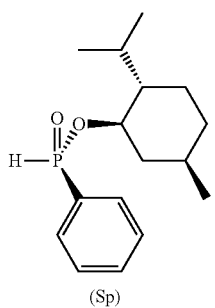 [SMILES: CC(C)[C@@H]1CC[C@@H](C)C[C@H]1O[P@H](=O)c1ccccc1]

(Sp)

To a solution of N-chlorosuccinimide (110 mg, 0.82 mmol, 1.5 equiv) in dichloromethane (5 mL) at −78° C. and under N$_2$ was added dropwise a solution of dimethyl sulfide (0.06 mL, 0.82 mmol, 1.5 equiv) in dichloromethane (1 mL). After 10 minutes at −78° C., a solution of 3a (170 mg, 0.55 mmol, 1 equiv) in dichloromethane (2 mL) was added over 20 minutes. After 1 h at −78° C., triethylamine (0.38 mL, 2.74 mmol, 5 equiv) was added over 15 minutes and the reaction was allowed to warm to rt. After 1 h at rt, water was added and the two layers were separated. The aqueous layer was then washed with dichloromethane (×2). The combined organic layer was dried over MgSO$_4$, filtered and concentrated under vacuum. The crude obtained was purified by column chromatography (hexane/ethyl acetate 6:4) to afford the product as a colorless oil (125 mg, 81%, de>99%). $^{31}$P NMR (121.47 MHz, CDCl$_3$): □=22.4 (d, J=557 Hz); $^1$H NMR (300 MHz, CDCl$_3$): □=7.67-7.82 (m, 2H), 7.68 (d, J=557 Hz, 1H), 7.42-7.62 (m, 3H), 4.18-4.32 (m, 1H), 2.25-2.35 (m, 1H), 2.02-2.16 (m, 1H), 1.62-1.75 (m, 2H), 1.22-1.58 (m, 3H), 0.80-1.14 (m, 2H), 0.95 (d, J=6.4 Hz, 3H), 0.88 (d, J=7.0 Hz, 3H), 0.67 (d, J=7.0 Hz, 3H)

(S$_p$)-Menthyl-1-naphtyl-H-phosphinate 4b

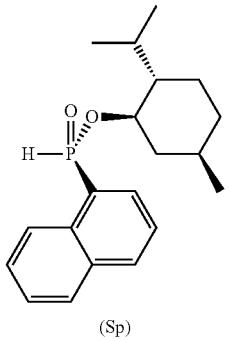 [SMILES: CC(C)[C@@H]1CC[C@@H](C)C[C@H]1O[P@H](=O)c1cccc2ccccc12]

(Sp)

To a solution of N-chlorosuccinimide (100 mg, 0.75 mmol, 3 equiv) in dichloromethane (15 mL) at −78° C. and under N$_2$ was added dropwise a solution of dimethyl sulfide (0.055 mL, 0.75 mmol, 3 equiv) in dichloromethane (2 mL). After 10 minutes at −78° C., a solution of 3c (90 mg, 0.25 mmol, 1 equiv) in dichloromethane (2 mL) was added over 20 minutes. After 1 h at −78° C., triethylamine (0.38 mL, 2.74 mmol, 5 equiv) was added over 15 minutes and the reaction was stirred for 30 minutes at −78° C. After warming up to rt, water was added and the two layers were separated. The aqueous layer was then washed with dichloromethane (×2). The combined organic layer was dried over MgSO$_4$, filtered and concentrated under vacuum. The crude obtained was purified by column chromatography (hexane/ethyl acetate 9:1 to 7:3) to afford the product as a colorless oil (72 mg, 87%, de=94%). $^{31}$P NMR (121.47 MHz, CDCl$_3$): □=23.3 (dm, J=557 Hz); $^1$H NMR (300 MHz, CDCl$_3$): □=8.45-8.51 (m, 1H), 7.99-8.10 (m, 2H), 8.05 (d, J=557 Hz, 1H), 7.90-7.96 (m, 1H), 7.54-7.67 (m, 3H), 4.31-4.44 (m, 1H), 2.34-2.44 (m, 1H), 2.05 (dquint., J=2.6 and 7.0 Hz, 1H), 1.61-1.74 (m, 2H), 1.24-1.56 (m, 3H), 0.97 (d, J=6.4 Hz, 3H), 0.75-1.10 (m, 2H), 0.80 (d, J=7.0 Hz, 3H), 0.61 (d, J=6.7 Hz, 3H); [α]$_D$=−73.97°

(S$_p$)-Menthyl methyl-H-phosphinate 4c

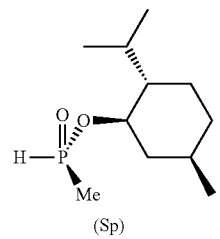

(Sp)

To a solution of N-chlorosuccinimide (470 mg, 3.5 mmol, 3 equiv) in dichloromethane (35 mL) at −78° C. and under N$_2$ was added dropwise a solution of dimethyl sulfide (0.26 mL, 3.5 mmol, 3 equiv) in dichloromethane (3 mL). After 10 minutes at −78° C., a solution of 2a (290 mg, 1.17 mmol, 1 equiv) in dichloromethane (5 mL) was added over 20 minutes. After 1 h at −78° C., triethylamine (0.81 mL, 5.84 mmol, 5 equiv) was added over 15 minutes and the reaction was stirred for 30 minutes at −78° C. After warming up to rt, water was added and the two layers were separated. The aqueous layer was then washed with dichloromethane (×2). The combined organic layer was dried over MgSO$_4$, filtered and concentrated under vacuum. The crude obtained was purified by column chromatography (hexane/ethyl acetate 8:2 to 4:6) to afford the product as a colorless oil (134 mg, 61%, de=96%). $^{31}$P NMR (121.47 MHz, CDCl$_3$): □=28.5 (dm, J=537 Hz); $^1$H NMR (300 MHz, CDCl$_3$): □=7.33 (d, J=537 Hz, 1H), 4.15-4.29 (m, 1H), 2.06-2.20 (m, 2H), 1.62-1.73 (m, 2H), 1.52 (d, J=15.2 Hz, 3H), 1.24-1.58 (m, 2H), 1.14 (q, J=11.4 Hz, 1H), 0.93 (d, J=6.2 Hz, 6H), 0.78-1.10 (m, 2H), 0.83 (d, J=7.1 Hz, 3H)

($S_p$)-Menthyl(hydroxymethyl)phenylphosphinate 5

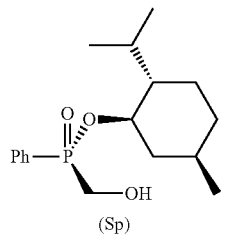 [SMILES: CC(C)[C@@H]1CC[C@@H](C)C[C@H]1O[P@](=O)(CO)c1ccccc1]

To a solution of phenylphosphinic acid (42.6 g, 300 mmol, 1 equiv) in toluene (300 mL) was added L-menthol (46.9 g, 300 mmol, 1 equiv). The reaction mixture was then stirred at reflux for 24 h under N$_2$ and in a flask equipped with a Dean-stark trap. After cooling down the reaction to rt, paraformaldehyde (9.01 g, 300 mmol, 1 equiv) was added and the reaction mixture was stirred at reflux for 24 h under N$_2$. The solvent was then removed under vacuum and the crude obtained was recrystallized at rt in diethyl ether (200 mL) to afford the product as colorless crystals (24.2 g, 26%, de=95%). Mp=138-139° C.; $^{31}$P NMR (121.47 MHz, CDCl$_3$): H=37.2 (s); $^1$H NMR (300 MHz, CDCl$_3$): □=7.77-7.87 (m, 2H), 7.52-7.60 (m, 1H), 7.42-7.51 (m, 2H), 4.29-4.43 (m, 2H), 3.93-4.10 (m, 2H), 2.26 (dquint., J=2.6 and 7.0 Hz, 1H), 1.80-1.91 (m, 1H), 1.57-1.73 (m, 2H), 1.26-1.47 (m, 2H), 0.96 (d, J=7.1 Hz, 3H), 0.74-1.13 (m, 3H), 0.89 (d, J=7.0 Hz, 3H), 0.78 (d, J=6.4 Hz, 3H); $^{13}$C NMR (75.46 MHz, CDCl$_3$): □□=132.3 (d, J$_{PCCCC}$=2.8 Hz), 131.7 (d, J$_{PCCC}$=9.9 Hz, 2C), 130.6 (d, J$_{PC}$=123 Hz), 128.3 (d, J$_{PCC}$=12.1 Hz, 2C), 77.1 (d, J$_{POC}$=8.3 Hz), 60.2 (d, J$_{PC}$=117 Hz), 48.7 (d, J$_{POCC}$=6.1 Hz), 43.2, 34.0, 31.4, 25.5, 22.8, 21.9, 21.1, 15.7; HRMS (EI+) m/z calcd for C$_{16}$H$_{28}$O$_3$P ([M+H]$^+$) 311.1776. found 311.1766; [α]$_D$=−46.74°

($R_R$)-Menthyl phenyl-H-phosphinate 6

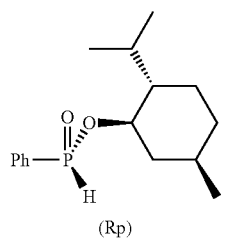 [SMILES: CC(C)[C@@H]1CC[C@@H](C)C[C@H]1O[P@@H](=O)c1ccccc1]

To a solution of N-chlorosuccinimide (1.6 g, 12 mmol, 3 equiv) in dichloromethane (80 mL) at −78° C. and under N$_2$ was added dropwise a solution of dimethyl sulfide (0.88 mL, 12 mmol, 3 equiv) in dichloromethane (5 mL). After 10 minutes at −78° C., a solution of 5 (1.24 g, 4 mmol, 1 equiv) in dichloromethane (10 mL) was added over 20 minutes. After 1 h at −78° C., triethylamine (2.8 mL, 20 mmol, 5 equiv) was added over 15 minutes and the reaction was stirred for 30 minutes at −78° C. After warming up to rt, water was added and the two layers were separated. The aqueous layer was then washed with dichloromethane (×2). The combined organic layer was dried over MgSO$_4$, filtered and concentrated under vacuum. The crude obtained was purified by column chromatography (hexane/ethyl acetate 9:1 to 8:2) to afford the product as a colorless oil (1.03 g, 91%, de=95%). $^{31}$P NMR (121.47 MHz, CDCl$_3$): □=24.7 (dm, J=553 Hz); $^1$H NMR (300 MHz, CDCl$_3$): □=7.73-7.84 (m, 2H), 7.66 (d, J=553 Hz, 1H), 7.46-7.64 (m, 3H), 4.22-4.36 (m, 1H), 2.14-2.27 (m, 2H), 1.62-1.75 (m, 2H), 1.38-1.54 (m, 2H), 1.24 (q, J=11.2 Hz, 1H), 0.78-1.13 (m, 2H), 0.96 (d, J=7.0 Hz, 3H), 0.90 (d, J=6.4 Hz, 3H), 0.86 (d, J=7.0 Hz, 3H); [α]$_D$=−35.48°

($S_p$)-Menthyl(p-anisyl)phenylphosphinate 7a

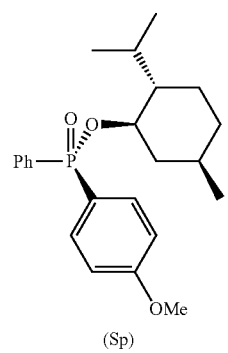 [SMILES: COc1ccc([P@@](=O)(O[C@@H]2C[C@H](C)CC[C@H]2C(C)C)c2ccccc2)cc1]

In a round bottom flask was introduced 6 (280.3 mg, 1 mmol, 1 equiv), Pd(OAc)$_2$ (4.5 mg, 0.02 mmol, 2.0 mol %), xantphos (12.7 mg, 0.022 mmol, 2.2 mol %), a mixture of toluene and ethyl glycol (4.5 mL:0.5 mL), DIPEA (0.23 mL, 1.3 mmol, 1.3 equiv) and 4-iodoanisole (234 mg, 1 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in ethyl acetate and washed with a saturated aqueous solution of NaHCO$_3$ and brine. The organic layer was dried over MgSO$_4$, filtered and concentrated under vacuum. The crude obtained was purified by column chromatography (hexane/ethyl acetate 8:2 to 7:3) to afford the product as a yellow oil (325 mg, 84%, de=97%). $^{31}$P NMR (121.47 MHz, CDCl$_3$): □=29.7 (s); $^1$H NMR (300 MHz, CDCl$_3$): □=7.67-7.86 (m, 4H), 7.38-7.54 (m, 3H), 6.90-6.98 (m, 2H), 4.15-4.28 (m, 1H), 3.84 (s, 3H), 2.06-2.23 (m, 2H), 1.58-1.70 (m, 2H), 1.30-1.51 (m, 2H), 1.21 (q, J=11.1 Hz, 1H), 0.78-1.04 (m, 2H), 0.89 (d, J=7.0 Hz, 3H), 0.85 (d, J=6.5 Hz, 3H), 0.55 (d, J=6.8 Hz, 3H); $^{13}$C NMR (75.46 MHz, CDCl$_3$): i=162.4 (d, J$_{PCCCC}$=3.3 Hz), 133.5 (d, J$_{PCCC}$=11.6 Hz, 2C), 133.4 (d, J$_{PC}$=139 Hz), 131.6 (d, J$_{PCCCC}$=2.8 Hz), 131.4 (d, J$_{PCCC}$=10.5 Hz, 2C), 128.2 (d, J$_{PCC}$=12.7 Hz), 123.4 (d, J$_{PC}$=143 Hz), 113.8 (d, J$_{PCC}$=13.8 Hz), 76.9 (d, J$_{POC}$=7.2 Hz), 55.1, 48.8 (d, J$_{POCC}$=6.6 Hz), 43.5, 34.0, 31.5, 25.5, 22.6, 21.9, 21.1, 15.3; HRMS (EI+) m/z calcd for C$_{23}$H$_{31}$O$_3$P ([M]$^+$) 386.2012. found 386.2015; [α]$_D$=−68.41°

(S_p)-Menthyl(o-anisyl)phenylphosphinate 7b

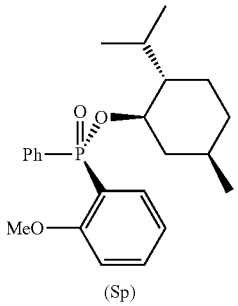 [SMILES: COc1ccccc1[P@@](=O)(O[C@@H]1C[C@H](C)CC[C@H]1C(C)C)c1ccccc1]
(Sp)

In a round bottom flask was introduced 6 (280.3 mg, 1 mmol, 1 equiv), Pd(OAc)$_2$ (4.5 mg, 0.02 mmol, 2.0 mol %), xantphos (12.7 mg, 0.022 mmol, 2.2 mol %), a mixture of toluene and ethyl glycol (4.5 mL:0.5 mL), DIPEA (0.23 mL, 1.3 mmol, 1.3 equiv) and 2-bromoanisole (0.125 mL, 1 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in ethyl acetate and washed with a saturated aqueous solution of NaHCO$_3$ and brine. The organic layer was dried over MgSO$_4$, filtered and concentrated under vacuum. The crude obtained was purified by column chromatography (hexane/ethyl acetate 9:1 to 7:3) to afford the product as a white solid (339 mg, 88%, de>99%). Mp=91-93° C.; $^{31}$P NMR (121.47 MHz, CDCl$_3$): □=27.6 (s); $^1$H NMR (300 MHz, CDCl$_3$): □=7.99-8.11 (m, 1H), 7.76-7.88 (m, 2H), 7.35-7.54 (m, 4H), 7.02-7.11 (m, 1H), 6.77-6.86 (m, 1H), 4.15-4.28 (m, 1H), 3.61 (s, 3H), 2.10-2.25 (m, 2H), 1.56-1.71 (m, 2H), 1.30-1.51 (m, 2H), 1.21 (q, J=11.2 Hz, 1H), 0.78-1.03 (m, 2H), 0.87 (d, J=7.1 Hz, 3H), 0.84 (d, J=6.4 Hz, 3H), 0.48 (d, J=6.7 Hz, 3H); [α]$_D$=−90.31°

(S_p)-Menthyl(o-anisyl)phenylphosphinate 7c

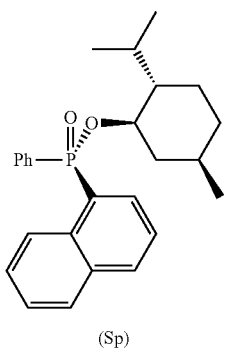 [SMILES: CC(C)[C@@H]1CC[C@@H](C)C[C@H]1O[P@@](=O)(c1ccccc1)c1cccc2ccccc12]
(Sp)

In a round bottom flask was introduced 6 (280.3 mg, 1 mmol, 1 equiv), Pd(OAc)$_2$ (4.5 mg, 0.02 mmol, 2.0 mol %), xantphos (12.7 mg, 0.022 mmol, 2.2 mol %), a mixture of toluene and ethyl glycol (4.5 mL:0.5 mL), DIPEA (0.23 mL, 1.3 mmol, 1.3 equiv) and 1-bromonaphthalene (0.14 mL, 1 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in ethyl acetate and washed with a saturated aqueous solution of NaHCO$_3$ and brine. The organic layer was dried over MgSO$_4$, filtered and concentrated under vacuum. The crude obtained was purified by column chromatography (hexane/ethyl acetate 9:1 to 8:2) to afford the product as a white solid (378 mg, 93%, de=93%). Mp=85-87° C.; $^{31}$P NMR (121.47 MHz, CDCl$_3$): □=29.6 (s); $^1$H NMR (300 MHz, CDCl$_3$): □=8.41-8.47 (m, 1H), 8.24-8.34 (m, 1H), 7.99-8.06 (m, 1H), 7.76-7.89 (m, 3H), 7.52-7.60 (m, 1H), 7.36-7.52 (m, 5H), 4.33-4.47 (m, 1H), 2.07-2.17 (m, 1H), 1.91-2.04 (m, 1H), 1.56-1.68 (m, 3H), 1.33-1.52 (m, 2H), 1.26 (q, J=10.8 Hz, 1H), 0.78-1.03 (m, 2H), 0.85 (d, J=6.2 Hz, 3H), 0.73 (d, J=7.1 Hz, 3H), 0.39 (d, J=6.7 Hz, 3H)

(R_p)-Menthyl methylphenylphosphinate 8a

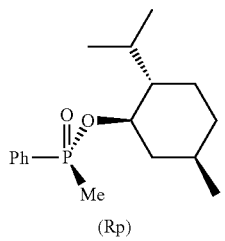 [SMILES: CC(C)[C@@H]1CC[C@@H](C)C[C@H]1O[P@@](C)(=O)c1ccccc1]
(Rp)

To a solution of 6 (280 mg, 1 mmol, 1 equiv) in dichloromethane (10 mL) at 0° C. and under N$_2$ was added bis(trimethylsilyl)acetamide (0.49 mL, 2 mmol, 2 equiv) followed by iodomethane (0.125 mL, 2 mmol, 2 equiv). The ice-bath was removed and the reaction mixture was stirred for 2 h at rt. Methanol was added (0.08 mL, 2 mmol, 2 equiv) and the reaction mixture was concentrated under vacuum. The residue obtained was dissolved in ethyl acetate and the organic layer was washed with a saturated aqueous solution of NaHCO$_3$ and brine. The organic layer was dried over MgSO$_4$, filtered and concentrated under vacuum. The crude obtained was purified by column chromatography (hexane/ethyl acetate 9:1 to 8:2) to afford the product as white solid (265 mg, 90%, de=94%). Mp=82-84° C.; $^{31}$P NMR (121.47 MHz, CDCl$_3$): □=39.5 (s); $^1$H NMR (300 MHz, CDCl$_3$): □=7.47-7.57 (m, 2H), 7.14-7.29 (m, 3H), 3.92-4.06 (m, 1H), 1.91 (dquint., J=2.6 and 6.7 Hz, 1H), 1.47-1.57 (m, 1H), 1.36 (d, J=14 Hz, 3H), 1.27-1.42 (m, 2H), 0.95-1.14 (m, 2H), 0.46-0.82 (m, 3H), 0.67 (d, J=7.0 Hz, 3H), 0.60 (d, J=7.0 Hz, 3H), 0.48 (d, J=6.4 Hz, 3H); [α]$_D$=−36.40°

(R_p)-Menthyl allylphenylphosphinate 8b

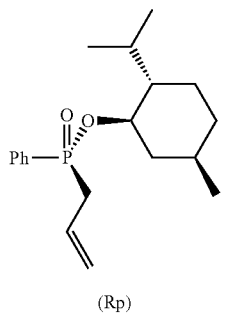 [SMILES: C=CC[P@@](=O)(O[C@@H]1C[C@H](C)CC[C@H]1C(C)C)c1ccccc1]
(Rp)

To a solution of 6 (520 mg, 1.85 mmol, 1 equiv) in dichloromethane (20 mL) at 0° C. and under $N_2$ was added bis(trimethylsilyl)acetamide (0.91 mL, 3.71 mmol, 2 equiv) followed by allyl bromide (0.32 mL, 3.71 mmol, 2 equiv). The ice-bath was removed and the reaction mixture was stirred for 4 days at rt. Methanol was added (0.15 mL, 3.71 mmol, 2 equiv) and the reaction mixture was concentrated under vacuum. The residue obtained was dissolved in ethyl acetate and the organic layer was washed with a saturated aqueous solution of $NaHCO_3$ and brine. The organic layer was dried over $MgSO_4$, filtered and concentrated under vacuum. The crude obtained was purified by column chromatography (hexane/ethyl acetate 9:1 to 7:3) to afford the product as yellow oil (336 mg, 57%, de=96%). $^{31}$P NMR (121.47 MHz, $CDCl_3$): $\square$=37.7 (s); $^1$H NMR (300 MHz, $CDCl_3$): $\square$=7.71-7.84 (m, 2H), 7.40-7.58 (m, 3H), 5.64-5.82 (m, 1H), 4.96-5.14 (m, 2H), 4.24-4.39 (m, 1H), 2.62-2.87 (m, 2H), 2.18-2.33 (m, 1H), 1.72-1.84 (m, 1H), 1.54-1.72 (m, 2H), 1.23-1.46 (m, 2H), 0.68-1.10 (m, 3H), 0.95 (d, J=7.0 Hz, 3H), 0.88 (d, J=6.7 Hz, 3H), 0.75 (d, J=6.5 Hz, 3H); $^{13}$C NMR (75.46 MHz, $CDCl_3$): $\square\square$=132.4 (d, $J_{PC}$=126 Hz), 131.8 (d, $J_{PCCCC}$=2.8 Hz), 131.4 (d, $J_{PCCC}$=10.0 Hz, 2C), 128.1 (d, $J_{PCC}$=12.7 Hz, 2C), 127.3 (d, $J_{PCCC}$=9.4 Hz), 120.0 (d, $J_{PCC}$=13.2 Hz), 76.4 (d, $J_{POC}$=7.2 Hz), 48.7 (d, $J_{POCC}$=6.0 Hz), 43.0, 36.6 (d, $J_{PC}$=97.3 Hz), 33.9, 31.3, 25.5, 22.7, 21.8, 21.0, 15.6; HRMS (EI+) m/z calcd for $C_{19}H_{29}O_2P$ ([M]$^+$) 320.1905. found 320.1912; [α]$_D$=−36.65°

($R_p$)-Menthyl octylphenylphosphinate 9

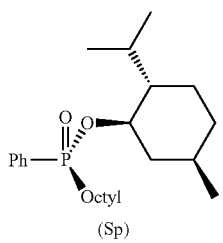

(Sp)

To a solution of 6 (375 mg, 1.34 mmol, 1 equiv) in hexane (5 mL) was added 1-octene (0.21 mL, 1.34 mmol, 1 equiv) followed by the addition of triethylborane (1.34 mL, 1.34 mmol, 1 equiv, 1.0M in THF). The reaction mixture was stirred for 20 h at rt under air. Ethyl acetate and an aqueous solution of $NaHSO_4$ at 1M were added and the two layers were separated. The organic layer was washed with $NaHCO_3$ and brine, dried over $MgSO_4$, filtered and concentrated under vacuum. The crude obtained was purified by column chromatography (hexane/ethyl acetate 90:15 to 85:15) to afford the product as yellow oil (384 mg, 73%, de=95%).

In a round bottom flask was introduced 6 (280 mg, 1 mmol, 1 equiv) 1-octene (0.39 mL, 2.5 mmol, 2.5 equiv) and $Mn(OAc)_2$ (9 mg, 0.05 mmol, 5 mol %). The reaction mixture was stirred for 16 h at 100° C. under air. Ethyl acetate and an aqueous solution of $Na_2S_2O_4$ at 0.5M were added and the two layers were separated. The organic layer was washed with brine, dried over $MgSO_4$, filtered and concentrated under vacuum. The crude obtained was purified by column chromatography (hexane/ethyl acetate 9:1 to 8:2) to afford the product as yellow oil (309 mg, 79%, de=95%). $^{31}$P NMR (121.47 MHz, $CDCl_3$): $\square$=42.4 (s); $^1$H NMR (300 MHz, $CDCl_3$): $\square$=7.73-7.84 (m, 2H), 7.41-7.56 (m, 3H), 4.22-4.35 (m, 1H), 2.25 (dquint., J=2.4 and 7.0 Hz, 1H), 1.48-1.98 (m, 5H), 1.13-1.48 (m, 14H), 0.70-1.10 (m, 3H), 0.96 (d, J=7.1 Hz, 3H), 0.88 (d, J=7.0 Hz, 3H), 0.86 (t, J=6.8 Hz, 3H), 0.74 (d, J=6.5 Hz, 3H); [α]$_D$=−27.42°

($S_p$)-Menthyl(N-methylphthalimide)phenylphosphinate 10

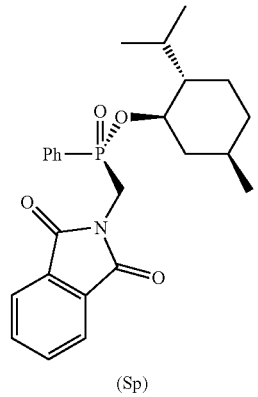 [SMILES: CC(C)[C@@H]1CC[C@@H](C)C[C@H]1O[P@](=O)(CN1C(=O)c2ccccc2C1=O)c1ccccc1]

(Sp)

To a solution of 5 (621 mg, 2 mmol, 1 equiv), phtalimide (382.5 mg, 2.6 mmol, 1.3 equiv) and diphenyl-2-pyridylphosphine (684.5 mg, 2.6 mmol, 1.3 equiv) in dichloromethane (20 ml) was added diisopropyl azodicarboxylate (0.51 mL, 2.6 mmol, 1.3 equiv). The reaction mixture was stirred for 24 h at rt under $N_2$. Water and brine (1:1) were added and the two layers were separated. The aqueous layer was then extracted with dichloromethane (×2). The combined organic layers was dried over $MgSO_4$, filtered and concentrated under vacuum. The residue obtained was purified by column chromatography (hexanes/ethyl acetate 9:1 to 7:3) to afford the product as a white solid (612 mg, 70%, de=95%). Mp=106-107° C.; $^{31}$P NMR (121.47 MHz, $CDCl_3$): $\square$=31.4 (s); $^1$H NMR (300 MHz, $CDCl_3$): $\square$=7.79-7.91 (m, 4H), 7.68-7.75 (m, 2H), 7.52-7.60 (m, 1H), 7.42-7.51 (m, 2H), 4.33-4.46 (m, 1H), 4.10-4.30 (m, 2H), 2.17 (dquint., J=2.3 and 6.7 Hz, 1H), 1.78-1.88 (m, 1H), 1.55-1.69 (m, 2H), 1.20-1.46 (m, 2H), 0.94-1.12 (m, 2H), 0.72-0.88 (m, 1H), 0.84 (d, J=7.0 Hz, 3H), 0.79 (d, J=7.0 Hz, 3H), 0.75 (d, J=6.8 Hz, 3H); $^{13}$C NMR (75.46 MHz, $CDCl_3$): $\square\square$=166.6 (2C), 134.0 (2C), 132.5 (d, $J_{PCCCC}$=2.8 Hz), 131.7 (2C), 131.6 (d, $J_{PCCC}$=8.8 Hz, 2C), 131.3 (d, $J_{PC}$=130 Hz), 128.3 (d, $J_{PCC}$=12.7 Hz, 2C), 123.2 (2C), 77.6 (d, $J_{POC}$=7.7 Hz), 48.5 (d, $J_{POCC}$=6.1 Hz), 42.9, 38.1 (d, $J_{PC}$=107 Hz), 33.8, 31.3, 25.3, 22.5, 21.8, 20.9, 15.4; HRMS (EI+) m/z calcd for $C_{25}H_{31}NO_4P$ ([M+H]$^+$) 440.1991. found 440.1985; [α]$_D$=−21.18°

($S_p$)-Menthyl[(tosyloxy)methyl]phenylphosphinate 11

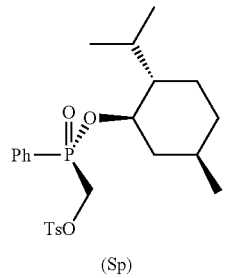 [SMILES: Cc1ccc(S(=O)(=O)OC[P@@](=O)(O[C@@H]2C[C@H](C)CC[C@H]2C(C)C)c2ccccc2)cc1]

(Sp)

To a solution of 5 (3.1 g, 10 mmol, 1 equiv) in dichloromethane (60 ml) under $N_2$ was added N,N-diisopropylethylamine (4.35 mL, 25 mmol, 2.5 equiv). The mixture was cooled down to 0° C. and a solution of tosyl chloride (2.89 g, 20 mmol, 2 equiv) in dichloromethane (45 ml) was added over 1 h. The ice-bath was removed and the solution was stirred for 20 h at rt. A saturated aqueous solution of $NaHCO_3$ was added and the two layers were separated. The aqueous layer was extracted with dichloromethane (2×). The combined organic layers was dried over $MgSO_4$, filtered and concentrated under vacuum. The residue obtained was purified by column chromatography (hexanes/ethyl acetate 9:1 to 7:3) to afford the product as colorless crystals (4.42 g, 95%, de=92%). Mp=68-70° C.; $^{31}$P NMR (121.47 MHz, $CDCl_3$): □=29.3 (s); $^1$H NMR (300 MHz, $CDCl_3$): □=7.72-7.82 (m, 2H), 7.56-7.64 (m, 3H), 7.42-7.52 (m, 2H), 7.23-7.29 (m, 2H), 4.09-4.42 (m, 3H), 2.44 (s, 3H), 2.14 (dquint., J=2.6 and 7.0 Hz, 1H), 1.90-2.00 (m, 1H), 1.57-1.73 (m, 2H), 1.26-1.48 (m, 2H), 1.11 (q, J=11.1 Hz, 1H), 0.76-1.06 (m, 2H), 0.93 (d, J=7.1 Hz, 3H), 0.80 (d, J=6.5 Hz, 3H), 0.80 (d, J=7.0 Hz, 3H); HRMS (EI+) m/z calcd for $C_{24}H_{34}O_5PS$ ([M+H]$^+$) 465.1865. found 465.1857; $[\alpha]_D$=−29.575°

($S_p$)-Menthyl(iodomethyl)phenylphosphinate 12

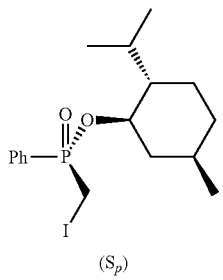 [SMILES: CC(C)[C@@H]1CC[C@@H](C)C[C@H]1O[P@](=O)(CI)c1ccccc1]

To a solution of 11 (2.32 g, 5 mmol, 1 equiv) in acetone (35 ml) was added sodium iodide (3.0 g, 20 mmol, 4 equiv). The reaction mixture was stirred for 24 h at reflux. The solvent was removed under vacuum and the residue obtained was dissolved in dichloromethane. The organic layer was washed with brine, dried over $MgSO_4$, filtered and concentrated under vacuum. The solid obtained was purified by column chromatography (dichloromethane/ethyl acetate 10:0 to 9:1) to afford the product as a yellow solid (1.612 g, 77%, de=91%). Mp=66-68° C.; $^{31}$P NMR (121.47 MHz, $CDCl_3$): □=32.1 (s); $^1$H NMR (300 MHz, $CDCl_3$): □=7.79-7.90 (m, 2H), 7.44-7.64 (m, 3H), 4.33-4.47 (m, 1H), 3.05-3.28 (m, 2H), 2.30-2.45 (m, 1H), 1.80-1.91 (m, 1H), 1.57-1.74 (m, 2H), 1.23-1.51 (m, 2H), 0.76-1.10 (m, 3H), 0.97 (d, J=7.1 Hz, 3H), 0.90 (d, J=7.1 Hz, 3H), 0.76 (d, J=6.8 Hz, 3H); $^{13}$C NMR (75.46 MHz, $CDCl_3$): □□=132.6 (d, $J_{PCCCC}$=2.7 Hz), 131.9 (d, $J_{PCCC}$=9.9 Hz, 2C), 130.3 (d, $J_{PC}$=136 Hz), 128.4 (d, $J_{PCC}$=13.2 Hz, 2C), 78.2 (d, $J_{POC}$=7.2 Hz), 48.7 (d, $J_{POCC}$=6.1 Hz), 43.1, 34.0, 31.4, 25.6, 22.9, 21.9, 21.2, 15.9, −6.5 (d, $J_{PC}$=102 Hz); HRMS (EI+) m/z calcd for $C_{17}H_{27}IO_2P$ ([M+H]$^+$) 421.0793. found 421.0793; $[\alpha]_D$=−29.46°

($R_p$, $R_p$)-Menthyl(methyl)phenylphosphinate 13

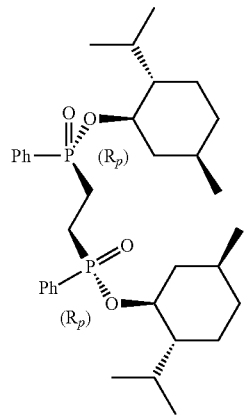

To a solution of 12 (420.3 mg, 1 mmol, 1 equiv) in THF (8 mL) at −78° C. under $N_2$ was slowly added isopropyl magnesium chloride (0.55 mL, 1.1 mmol, 1.1 equiv, 2.0M in THF). After 1 h of stirring at −78° C., $CuCl_2$ (403 mg, 3 mmol, 3 equiv) was added. The ice-bath was removed and the reaction mixture was stirred for 2 h at rt. A saturated solution of $NH_4Cl$ was added and the two layers were separated. The aqueous layer was extracted with dichloromethane (3×). The combined organic layers was dried over $MgSO_4$, filtered and concentrated under vacuum. The crude obtained was purified by column chromatography (hexane/ethyl acetate 8:2 to 6:4) to afford the product as a white solid (237 mg, 81%, de=92%). Mp=84-85° C.; $^{31}$P NMR (121.47 MHz, $CDCl_3$): □=39.7 (m); $^1$H NMR (300 MHz, $CDCl_3$): □=7.77-7.87 (m, 4H), 7.44-7.59 (m, 6H), 4.23-4.36 (m, 2H), 2.21 (dquint., J=2.3 and 7.0 Hz, 2H), 1.78-1.87 (m, 2H), 1.66 (d, J=14.4 Hz, 4H), 1.56-1.72 (m, 4H), 1.25-1.44 (m, 4H), 0.74-1.11 (m, 6H), 0.97 (d, J=7.1 Hz, 6H), 0.90 (d, J=7.0 Hz, 6H), 0.78 (d, J=6.4 Hz, 6H); $[\alpha]_D$=−24.825°

General Wittig-Rearrangement Procedure:

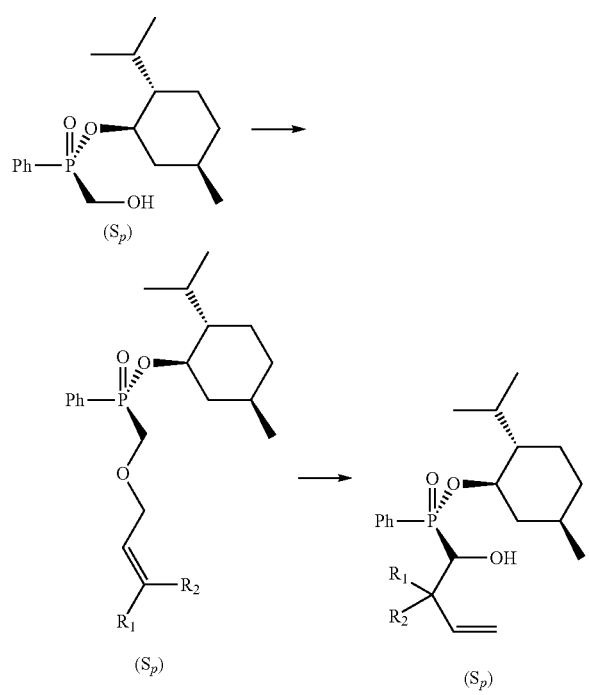

To a suspension of NaH (120 mg, 3 mmol, 1.5 equiv, 60% in mineral oil) in THF (15 mL) at 0° C. under $N_2$ was added a solution of 5 (621 mg, 2 mmol, 1 equiv) in THF (5 mL). After 30 minutes of stirring at 0° C., a solution of the appropriate allyl bromide (2.4 mmol, 1.2 equiv) in THF (3 mL) was added. The reaction mixture was stirred for 16 h at rt. A saturated solution of $NH_4Cl$ was added and the two layers were separated. The aqueous layer was extracted with dichloromethane (3×). The combined organic layers was dried over $MgSO_4$, filtered and concentrated under vacuum. The pure intermediate was obtained directly after extraction or after purification by column chromatography (hexane/ethyl acetate).

To a solution of the purified intermediate (1 equiv) in THF at −78° C. under $N_2$ was slowly added a solution of sec-BuLi (2 equiv, 1.4M in cyclohexane). After 24 hours at −78° C., a saturated solution of $NH_4Cl$ was added and the two layers were separated. The aqueous layer was extracted with dichloromethane (3×). The combined organic layers was dried over $MgSO_4$, filtered and concentrated under vacuum. The crude was purified by column chromatography (hexane/ethyl acetate) to afford the appropriate product.

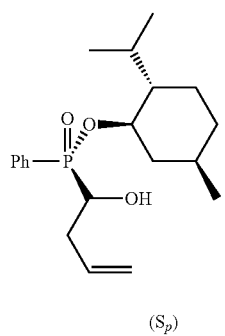 [SMILES: C=CCC(O)[P@@](=O)(O[C@@H]1C[C@H](C)CC[C@H]1C(C)C)c1ccccc1]

($S_p$)

General wittig-rearrangement procedure using allyl bromide (0.21 mL, 2.4 mmol, 1.2 equiv). The pure intermediate was obtained as a colorless oil directly after extraction (455 mg, 65%, de>99%). $^{31}P$ NMR (121.47 MHz, $CDCl_3$): $\delta$=34.3 (s); $^1H$ NMR (300 MHz, $CDCl_3$): $\delta$=7.79-7.92 (m, 2H), 7.41-7.62 (m, 3H), 5.71-5.84 (m, 1H), 5.17-5.23 (m, 2H), 4.32-4.43 (m, 1H), 3.74-4.06 (m, 4H), 2.14-2.38 (m, 2H), 1.92-2.03 (m, 2H), 0.64-1.75 (m, 5H), 0.93 (d, J=7.0 Hz, 3H), 0.91 (d, J=6.4 Hz, 3H), 0.81 (d, J=6.7 Hz, 3H).

The second step was performed using the intermediate (350 mg, 1 mmol, 1 equiv) and sec-BuLi (1.43 mL, 2 mmol, 2 equiv, 1.4M in cyclohexane). The crude obtained was purified by column chromatography (hexane/ethyl acetate 9:1 to 7:3) to afford the product as a white solid (192 mg, 55%, de>99%). Mp=109-110° C.; $^{31}P$ NMR (121.47 MHz, $CDCl_3$): $\delta$=38.0 (s); $^1H$ NMR (300 MHz, $CDCl_3$): $\delta$=7.79-7.90 (m, 2H), 7.54-7.62 (m, 1H), 7.45-7.54 (m, 2H), 5.73-5.90 (m, 1H), 5.05-5.15 (m, 2H), 4.33-4.47 (m, 1H), 3.89-3.99 (m, 1H), 2.12-2.50 (m, 4H), 1.83-1.93 (m, 1H), 1.56-1.74 (m, 2H), 1.23-1.52 (m, 2H), 0.74-1.14 (m, 3H), 0.96 (d, J=6.7 Hz, 3H), 0.89 (d, J=6.8 Hz, 3H), 0.78 (d, J=6.5 Hz, 3H); $^{13}C$ NMR (75.46 MHz, $CDCl_3$): $\delta\delta$=134.4 (d, $J_{PCC}$=14.4 Hz), 132.4 (d, $J_{PCCC}$=9.4 Hz, 2C), 132.3 (d, $J_{PCCCC}$=2.3 Hz), 130.0 (d, $J_{PC}$=120 Hz), 128.2 (d, $J_{PCC}$=12.2 Hz, 2C), 117.4, 77.4 (d, $J_{POC}$=8.3 Hz), 70.2 (d, $J_{PC}$=115 Hz), 48.8 (d, $J_{POCC}$=6.0 Hz), 43.3, 35.7 (d, $J_{PCC}$=5.0 Hz), 34.0, 31.4, 25.7, 22.8, 21.9, 21.1, 15.7; HRMS (EI+) m/z calcd for $C_{20}H_{31}O_3P$ ([M+H]$^+$) 351.2089. found 351.2091; [α]$_D$=−34.00°

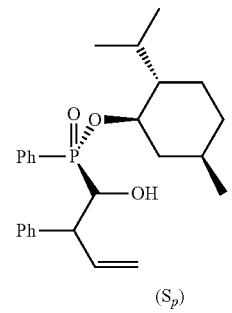 [SMILES: C=CC(c1ccccc1)C(O)[P@@](=O)(O[C@@H]1C[C@H](C)CC[C@H]1C(C)C)c1ccccc1]

($S_p$)

General wittig-rearrangement procedure using cinnamyl bromide (0.36 mL, 2.4 mmol, 1.2 equiv). The crude was purified by column chromatography (hexane/ethyl acetate 9:1 to 7:3) to afford the intermediate as a yellow oil (726 mg, 85%, de>99%). $^{31}P$ NMR (121.47 MHz, $CDCl_3$): $\delta$=35.0 (s); $^1H$ NMR (300 MHz, $CDCl_3$): $\delta$=7.83-7.93 (m, 2H), 7.53-7.60 (m, 1H), 7.43-7.53 (m, 2H), 7.22-7.36 (m, 5H), 6.50 (d, J=15.8 Hz, 1H), 6.07-6.19 (m, 1H), 4.32-4.45 (m, 1H), 4.19 (d, J=6.2 Hz, 2H), 3.81-3.99 (m, 2H), 2.24-2.36 (m, 1H), 1.93-2.03 (m, 1H), 1.57-1.74 (m, 2H), 1.22-1.50 (m, 2H), 1.11 (q, J=11.7 Hz, 1H), 0.74-1.06 (m, 2H), 0.95 (d, J=7.0 Hz, 3H), 0.87 (d, J=7.0 Hz, 3H), 0.80 (d, J=6.5 Hz, 3H); $^{13}C$ NMR (75.46 MHz, $CDCl_3$): $\delta\delta$=136.5, 133.5, 132.5 (d, $J_{PCCC}$=2.3 Hz), 132.0 (d, $J_{PCCC}$=9.4 Hz, 2C), 131.4 (d, $J_{PC}$=149 Hz), 128.7 (2C), 128.5 (d, $J_{PCC}$=13.3 Hz, 2C), 128.0, 126.7 (2C), 125.0, 77.4 (d, $J_{POC}$=7.5 Hz), 73.8 (d, $J_{PCOC}$=11.8 Hz), 67.3 (d, $J_{PC}$=119 Hz), 48.9 (d, $J_{POCC}$=6.0 Hz), 43.7, 34.2, 31.7, 25.8, 23.1, 22.1, 21.3, 16.0

The second step was performed using the intermediate (700 mg, 1.64 mmol, 1 equiv) and sec-BuLi (2.34 mL, 3.28 mmol, 2 equiv, 1.4M in cyclohexane). The crude obtained was purified by column chromatography (hexane/ethyl acetate 9:1 to 7:3) to afford the product as a white solid (532 mg, 76%, de>99%). Mp=103-105° C.; HRMS (EI+) m/z calcd for $C_{26}H_{36}O_3P$ ([M+H]$^+$) 427.2409. found 427.2401; [α]$_D$=−14.525°

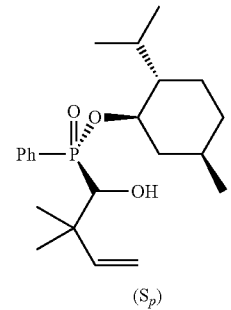 [SMILES: C=CC(C)(C)C(O)[P@@](=O)(O[C@@H]1C[C@H](C)CC[C@H]1C(C)C)c1ccccc1]

($S_p$)

General wittig-rearrangement procedure using prenyl bromide (0.31 mL, 2.4 mmol, 1.2 equiv). The crude was purified by column chromatography (hexane/ethyl acetate 9:1 to 8:2) to afford the intermediate as a colorless oil (734 mg, 97%, de=97%). $^{31}P$ NMR (121.47 MHz, $CDCl_3$): $\delta$=34.1 (s); $^1H$ NMR (300 MHz, $CDCl_3$): $\delta$=7.82-7.91 (m, 2H), 7.42-7.59 (m, 3H), 5.15-5.24 (m, 1H), 4.29-4.43 (m, 1H), 4.02 (d, J=6.7 Hz, 2H), 3.73-3.92 (m, 2H), 2.28 (dquint., J=2.4 and 7.0 Hz, 1H), 1.93-2.02 (m, 1H), 1.71 (s, 3H), 1.57-1.74 (m, 2H), 1.60 (s, 3H), 1.28-1.48 (m, 2H), 1.10 (q, J=11.1 Hz, 1H), 0.74-1.06 (m, 2H), 0.95 (d, J=7.0 Hz, 3H), 0.87 (d, J=6.8 Hz, 3H), 0.80

(d, J=6.5 Hz, 3H); $^{13}$C NMR (75.46 MHz, CDCl$_3$): □□=137.9, 132.1 (d, $J_{PCCCC}$=2.8Hz), 131.6 (d, $J_{PCCC}$=10.0 Hz, 2C), 131.2 (d, $J_{PC}$=128 Hz), 128.0 (d, $J_{PCC}$=12.7 Hz, 2C), 120.1, 76.9 (d, $J_{POC}$=7.7 Hz), 69.2 (d, $J_{PCOC}$=11.6 Hz), 66.5 (d, $J_{PC}$=119 Hz), 48.6 (d, $J_{POCC}$=6.1 Hz), 43.3, 33.9, 31.3, 25.6, 25.4, 22.7, 21.8, 21.0, 17.8, 15.6

The second step was performed using the intermediate (378.5 mg, 1 mmol, 1 equiv) and sec-BuLi (1.43 mL, 2 mmol, 2 equiv, 1.4M in cyclohexane). The crude obtained was purified by column chromatography (hexane/ethyl acetate 9:1 to 8:2) to afford the product as a white solid (244 mg, 64%, de>99%). Mp=130-131° C.; $^{31}$P NMR (121.47 MHz, CDCl$_3$): □=34.7 (s); $^1$H NMR (300 MHz, CDCl$_3$): □=7.82-7.92 (m, 2H), 7.51-7.59 (m, 1H), 7.41-7.50 (m, 2H), 5.88 (dd, J=10.7 and 17.3 Hz, 1H), 4.87-4.97 (m, 2H), 4.22-4.35 (m, 1H), 3.68 (s, 1H), 2.75 (s, 1H), 2.36 (dquint., J=2.1 and 7.0 Hz, 1H), 1.55-1.80 (m, 3H), 1.33-1.46 (m, 1H), 1.20-1.33 (m, 1H), 1.09 (s, 3H), 1.08 (s, 3H), 0.70-1.13 (m, 3H), 0.95 (d, J=7.0 Hz, 3H), 0.86 (d, J=7.0 Hz, 3H), 0.74 (d, J=6.5 Hz, 3H); $^{13}$C NMR (75.46 MHz, CDCl$_3$): □□=140.0 (d, $J_{PCCC}$=5.6 Hz), 132.9 (d, $J_{PC}$=119 Hz), 132.4 (d, $J_{PCCC}$=9.4 Hz, 2C), 132.1 (d, $J_{PCCCC}$=2.2 Hz), 128.0 (d, $J_{PCC}$=12.2 Hz, 2C), 112.7, 78.0 (d, $J_{PC}$=108 Hz), 77.3 (d, $J_{POC}$=8.3 Hz), 48.8 (d, $J_{POCC}$=5.0 Hz), 43.1, 41.3 (d, $J_{POCC}$=3.8 Hz), 33.9, 31.4, 25.3, 24.4 (d, $J_{PCCC}$=5.0 Hz), 23.7 (d, $J_{PCCC}$=6.7 Hz), 22.6, 21.9, 21.2, 15.5; HRMS (EI+) m/z calcd for C$_{22}$H$_{36}$O$_3$P ([M+H]$^+$) 379.2402. found 379.2405; [α]$_D$=-15.46°

($R_p$)-Methyl cinnamyl(hydroxymethyl)phosphinate 15

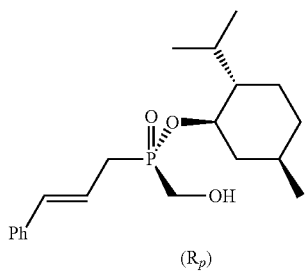 [SMILES: CC(C)[C@@H]1CC[C@@H](C)C[C@H]1O[P@](=O)(CO)C/C=C/c1ccccc1]

($R_p$)

In a round bottom flask was introduced 1 (234 mg, 1 mmol, 1 equiv), Pd(OAc)$_2$ (4.5 mg, 0.02 mmol, 2.0 mol %), xantphos (12.7 mg, 0.022 mmol, 2.2 mol %), a mixture of DMF and 1,2-dimethoxyethane (4.5 mL:0.5 mL), DIPEA (0.23 mL, 1.3 mmol, 1.3 equiv) and cinnamyl acetate (0.17 mL, 1 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in EtOAc and washed with a saturated aqueous solution of NaHCO$_3$ and brine. The organic layer was dried over MgSO$_4$, filtered and concentrated under vacuum. The crude obtained was purified by column chromatography (hexane/ethyl acetate 3:7 to 2:8) to afford the product as a white solid (55 mg, 16%, de=97%).

To a solution of cinnamylphosphinic acid (9.11 g, 50 mmol, 1 equiv) in toluene (100 mL) was added L-menthol (7.81 g, 50 mmol, 1 equiv). The reaction mixture was then stirred at reflux for 24 h under N$_2$ and in a flask equipped with a Dean-stark trap. After cooling down the reaction to rt, paraformaldehyde (1.5 g, 50 mmol, 1 equiv) was added and the reaction mixture was stirred at reflux for 24 h under N$_2$. The solvent was then removed under vacuum and the crude obtained was recrystallized at rt in a mixture ethyl acetate/diethyl ether (30 mL:150 mL) to afford the product as a white solid (5.6 g, 32%, de>99%). Mp=145-146° C.; $^{31}$P NMR (121.47 MHz, CDCl$_3$): □=48.8 (s); $^1$H NMR (300 MHz, CDCl$_3$): □=7.19-7.39 (m, 5H), 6.55 (dd, J=4.7 and 15.8 Hz, 1H), 6.12-6.27 (m, 1H), 4.20-4.34 (m, 1H), 3.87 (s, 2H), 3.64 (s, 1H), 2.85 (dd, J=7.6 and 17.6 Hz, 2H), 2.06-2.22 (m, 2H), 1.60-1.71 (m, 2H), 1.28-1.54 (m, 2H), 1.15 (q, J=11.7 Hz, 1H), 0.74-1.07 (m, 2H), 0.91 (d, J=6.4 Hz, 3H), 0.86 (d, J=6.8 Hz, 3H), 0.77 (d, J=7.0 Hz, 3H); $^{13}$C NMR (75.46 MHz, CDCl$_3$): □□=136.8 (d, $J_{PCCCC}$=3.3 Hz), 135.0 (d, $J_{PCC}$=12.2 Hz), 128.5 (2C), 127.5, 126.2 (d, $J_{PCCCCC}$=1.7 Hz, 2C), 118.4 (d, $J_{PCCC}$=10.5 Hz), 76.7 (d, $J_{POC}$=8.3 Hz), 59.5 (d, $J_{PC}$=106 Hz), 48.6 (d, $J_{POCC}$=5.6 Hz), 43.5, 34.0, 31.6 (d, $J_{PC}$=87.3 Hz), 31.5, 25.5, 22.7, 22.1, 21.0, 15.5; HRMS (EI+) m/z calcd for C$_{20}$H$_{31}$O$_3$P ([M]$^+$) 350.2011. found 350.2012; [α]$_D$=-51.60°

($R_p$)-Methyl cinnamyl-H-phosphinate 16

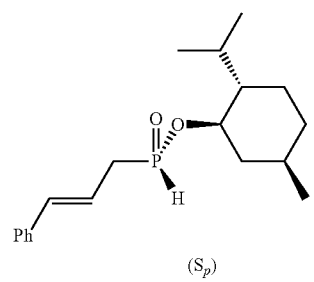 [SMILES: CC(C)[C@@H]1CC[C@@H](C)C[C@H]1O[P@@H](=O)C/C=C/c1ccccc1]

($S_p$)

To a solution of N-chlorosuccinimide (200 mg, 1.5 mmol, 3 equiv) in dichloromethane (20 mL) at -78° C. and under N$_2$ was added dropwise a solution of dimethyl sulfide (0.11 mL, 1.5 mmol, 3 equiv) in dichloromethane (3 mL). After 10 minutes at -78° C., a solution of 15 (175 mg, 0.5 mmol, 1 equiv) in dichloromethane (3 mL) was added over 20 minutes. After 1 h at -78° C., triethylamine (0.35 mL, 2.5 mmol, 5 equiv) was added over 15 minutes and the reaction was stirred for 30 minutes at -78° C. After warming up to rt, water was added and the two layers were separated. The aqueous layer was then washed with dichloromethane (×2). The combined organic layer was dried over MgSO$_4$, filtered and concentrated under vacuum. The crude obtained was purified by column chromatography (hexane/ethyl acetate 9:1 to 7:3) to afford the product as a colorless oil (132 mg, 82%, de>99%). $^{31}$P NMR (121.47 MHz, CDCl$_3$): □=30.9 (dm, J=539 Hz); $^1$H NMR (300 MHz, CDCl$_3$): □=7.20-7.41 (m, 5H), 7.17 (d, J=539 Hz, 1H), 6.56 (dd, J=5.9 and 15.8 Hz, 1H), 6.05-6.20 (m, 1H), 4.37-4.63 (m, 1H), 2.80 (dd, J=7.6 and 18.5 Hz, 2H), 2.06-2.24 (m, 2H), 1.62-1.73 (m, 2H), 1.34-1.55 (m, 2H), 1.15 (q, J=11.4 Hz, 1H), 0.75-1.12 (m, 2H), 0.92 (d, J=6.5 Hz, 3H), 0.91 (d, J=7.0 Hz, 3H), 0.82 (d, J=7.0 Hz, 3H); $^{13}$C NMR (75.46 MHz, CDCl$_3$): □□=136.8 (d, $J_{PCCCC}$=3.3 Hz), 135.8 (d, $J_{PCC}$=14.4 Hz), 128.6 (d, J=1.1 Hz, 2C), 127.8, 126.2 (d, $J_{PCCCCC}$=2.3 Hz, 2C), 117.0 (d, $J_{PCCC}$=10.0 Hz), 77.3 (d, $J_{POC}$=7.8 Hz), 48.4 (d, $J_{POCC}$=6.1 Hz), 41.8, 34.3 (d, $J_{PC}$=91.8 Hz), 34.0, 31.4, 25.7, 23.1, 21.9, 20.8, 15.8; HRMS (EI+) m/z calcd for C$_{19}$H$_{29}$O$_2$P ([M]$^+$) 320.1905. found 320.1907; [α]$_D$=-89.75°

(R$_p$)-Menthyl(acetylmethyl)-H-phosphinate 17

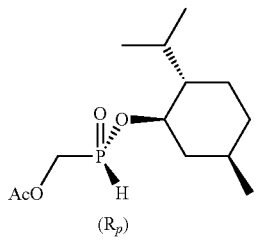 [SMILES: CC(=O)OC[P@H](=O)O[C@@H]1C[C@H](C)CC[C@H]1C(C)C]

To a solution of 1 (234 mg, 1 mmol, 1 equiv) in dichloromethane (3 mL) at 0° C. under N$_2$ was added triethylamine (0.17 mL, 1.2 mmol, 1.2 equiv) and acetic anhydride (0.10 mL, 1.1 mmol, 1.1 equiv).

The ice-bath was removed and the reaction mixture was stirred for 16 h at rt. The solvent was removed under vacuum and the residue obtained was solubilized in ethyl acetate. The organic layer was washed with NaHCO$_3$ and brine, dried over MgSO$_4$, filtered and concentrated under vacuum to afford the product as a white solid (272 mg, 98%, de=95%). $^{31}$P NMR (121.47 MHz, CDCl$_3$): □=26.8 (dm, J=567 Hz); $^1$H NMR (300 MHz, CDCl$_3$): □=7.32 (d, J=567 Hz, 1H), 4.28-4.37 (m, 2H), 4.09-4.24 (m, 1H), 2.18-2.27 (m, 1H), 2.14 (s, 3H), 1.96-2.12 (m, 1H), 1.62-1.74 (m, 2H), 1.36-1.54 (m, 2H), 1.28 (q, J=11.4 Hz, 1H), 0.76-1.11 (m, 2H), 0.93 (d, J=7.0 Hz, 6H), 0.80 (d, J=7.0 Hz, 3H); $^{13}$C NMR (75.46 MHz, CDCl$_3$): □□=170.0 (d, J$_{PCOC}$=6.0 Hz), 79.6 (d, J$_{POC}$=7.8 Hz), 60.0 (d, J$_{PC}$=113 Hz), 48.3 (d, J$_{POCC}$=6.1 Hz), 43.2, 33.6, 31.4, 25.4, 22.7, 21.7, 20.7, 20.1, 15.6

(R$_p$)-Menthyl(acetylmethyl)octylphosphinate 18

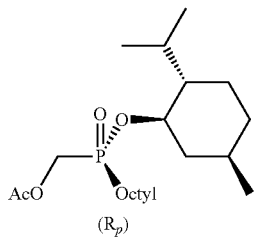

In a round bottom flask was introduced 17 (280 mg, 1 mmol, 1 equiv) 1-octene (0.39 mL, 2.5 mmol, 2.5 equiv) and Mn(OAc)$_2$ (9 mg, 0.05 mmol, 5 mol %). The reaction mixture was stirred for 16 h at 100° C. under air. Ethyl acetate and an aqueous solution of Na$_2$S$_2$O$_4$ at 0.5M were added and the two layers were separated. The organic layer was washed with brine, dried over MgSO$_4$, filtered and concentrated under vacuum. The crude obtained was purified by column chromatography (hexane/ethyl acetate 8:2 to 7:3) to afford the product as white solid (218 mg, 57%, de=88%). Mp=57-59° C.; [α]$_D$=−34.59°

Recycling of the Left Over of the Mixture of (Rp) and (Sp) of 1

(S$_p$)-Menthyl(hydroxymethyl)phenylphosphinate 5

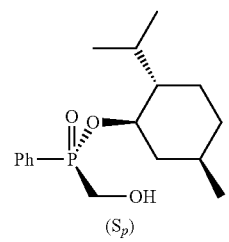 [SMILES: CC(C)[C@@H]1CC[C@@H](C)C[C@H]1O[P@](=O)(CO)c1ccccc1]

In a round bottom flask was introduced 1 (11.7 g, 50 mmol, 1 equiv, mixture of the two diastereoisomers 50:50), Pd(OAc)$_2$ (225 mg, 1 mmol, 2.0 mol %), xantphos (637 mg, 1.1 mmol, 2.2 mol %), a mixture of DMF and 1,2-dimethoxyethane (225 mL:25 mL), DIPEA (11.3 mL, 65 mmol, 1.3 equiv) and bromobenzene (5.26 mL, 50 mmol, 1 equiv). The reaction mixture was stirred under a flow of N$_2$ for 10 minutes and then heated at 115° C. for 24 hours before cooling to rt. The solvent was then removed under vacuum and the resulting residue was dissolved in EtOAc and washed with a saturated aqueous solution of NaHCO$_3$ and brine. The organic layer was dried over MgSO$_4$, filtered and concentrated under vacuum. The crude obtained was purified by column chromatography (hexane/ethyl acetate 5:5 to 3:7) to give a mixture of the two diastereoisomers (1:1). The residue was recrystallized using diethyl ether (100 mL) at rt to afford the product as a white solid (3.7 g, 24%, de=97%). Mp=103-105° C.; $^{31}$P NMR (121.47 MHz, CDCl$_3$): □=37.4 (s); $^1$H NMR (300 MHz, CDCl$_3$): □=7.80-7.91 (m, 2H), 7.45-7.62 (m, 3H), 4.09-4.21 (m, 1H), 4.02-4.08 (m, 2H), 2.77-2.87 (m, 1H), 2.29-2.39 (m, 1H), 1.90-2.05 (m, 1H), 1.58-1.69 (m, 3H), 1.22-1.50 (m, 2H), 0.93 (d, J=6.2 Hz, 3H), 0.85 (d, J=7.0 Hz, 3H), 0.76-1.02 (m, 2H), 0.47 (d, J=7.0 Hz, 3H); $^{13}$C NMR (75.46 MHz, CDCl$_3$): □□=132.3 (d, J$_{PCCCC}$=2.7 Hz), 131.8 (d, J$_{PCCC}$=9.9 Hz, 2C), 129.4 (d, J$_{PC}$=124 Hz), 128.4 (d, J$_{PCC}$=12.1 Hz, 2C), 77.4 (d, J$_{POC}$=8.3 Hz), 60.4 (d, J$_{PC}$=115 Hz), 48.6 (d, J$_{POCC}$=6.0 Hz), 43.6, 34.0, 31.5, 25.4, 22.6, 22.0, 21.0, 15.2; HRMS (EI+) m/z calcd for C$_{17}$H$_{27}$O$_3$P ([M+H]$^+$) 311.1776. found 311.1773; [α]$_D$=−44.58°

The process of the invention for the synthesis of asymmetric non-racemic P-chiral compounds is simple and inexpensive as compared to the known prior art processes. For example, with respect to the Mislow/Han process, the advantages are obvious:

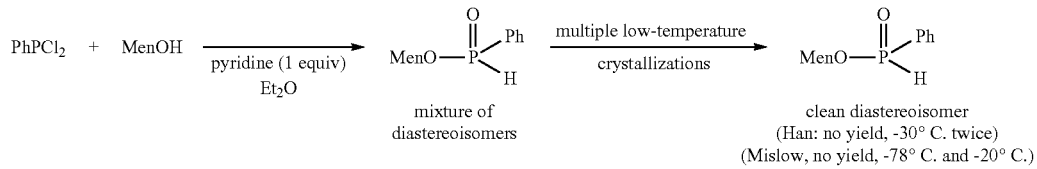

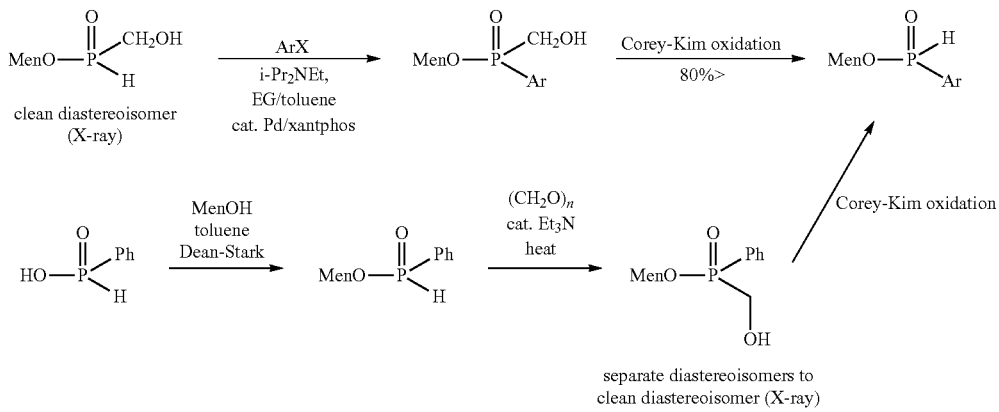

In summary, an invention has been provided that offers several advantages. The present invention easily handles the synthesis of either ($R_P$)- and ($S_P$)-PhP(O)(OMen)H without tedious crystallization at inconvenient temperatures, does not use PhCl2, does not use (+)-menthol, and can be easily applied to numerous other cases (different from a phenyl substituent). Applicants have prepared two versatile and inexpensive P-chiral building blocks 2 and 3. These are obtained in multigram quantities through simple and practical crystallization conditions, not relying on any chlorophosphine intermediate. The synthetic flexibility is illustrated with the preparation of both ($R_P$)-1 and ($S_P$)-1 from (−)-menthol. The presence of the hydroxymethyl group not only eases the crystallization process, but also offers the possibility to maintain the methylene carbon in other P-chiral derivatives, if desired. Compound 2 represents a novel chiral version of hypophosphorous esters, from which virtually any organophosphorus compound can be synthesized. The presently disclosed methodology represents a leap forward toward the general synthesis of P-chiral compounds.

While the invention has been shown in several of its forms, it is not thus limited but is susceptible to various changes and modifications without departing from the spirit thereof.

What is claimed is:

1. A P-chiral building block useful in the preparation of a variety of P-chiral organophosphorus compounds without using halogenated phosphorus starting materials, the building block having the formula:

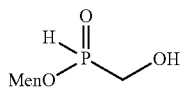

wherein the P-chiral building block is made from -(−) menthol as a starting material.

2. A P-chiral building block useful in the preparation of a variety of P-chiral organophosphorus compounds without using halogenated phosphorus starting materials, the building block having the formula:

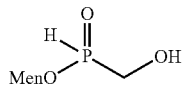

wherein the P-chiral building block is made from -(−) menthol as a starting material.

3. A P-chiral compound of the formula:

where R=H, Ph, aryl, alkyl, cinnamyl and R*=menthol; wherein the compound is made from a starting material having the formula:

the starting material being crystallized at about −18° C.

4. A P-chiral compound of the formula:

where R=H, Ph, aryl, alkyl, cinnamyl and R*=menthol; wherein the compound is made from a starting material having the formula:

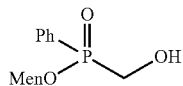

the starting material being crystallized at room temperature.

5. The P-chiral compound of claim 3, wherein the compound is made by reacting (−)-menthol, $H_3PO_2$ and paraformaldehyde.

6. The P-chiral compound of claim 4, wherein the compound is made by reacting phenyl-H-phosphinic acid, (−)-menthol and paraformaldehyde.

7. A process for the synthesis of asymmetric non-racemic P-chiral compound of the formula:

RP(O)(OR*)CH2OH where R=H, Ph, aryl, alkyl, cinnamyl and R*=menthol;

wherein the P-chiral compound is made by reacting (−)-menthol, $H_3PO_2$ and paraformaldehyde as reactants, followed by crystallization between room temperature and about −18° C. to produce a given yield for the process.

8. The process of claim 7, being further characterized by the absence of halogenated phosphorus starting materials.

9. The process of claim 5, wherein the P-chiral compound is crystallized at room temperature or in a simple freezer.

10. The process of claim 7, wherein the initial reactants make up a mother liquor, and wherein the yield of the process is improved by cross-coupling the mother liquor followed by crystallization.

11. A P-chiral compound of the formula:

$$RP(O)(OR^*)CH_2OH$$

where R=H, Ph, aryl, alkyl, cinnamyl and R*=a chiral alcohol selected from the group consisting of menthol, (1R)-endo-(+)-fenchyl alcohol, (−)-borneol and D-(−)-pantolactone.

\* \* \* \* \*